United States Patent [19]

Kirsch et al.

[11] 4,300,015
[45] Nov. 10, 1981

[54] CRYSTALLINE ALUMINO-SILICATE ZEOLITES CONTAINING POLYVALENT METAL CATIONS

[75] Inventors: Francis W. Kirsch, Wayne; David S. Barmby, Media; John D. Potts, Springfield, all of Pa.

[73] Assignee: Sun Oil Company of Pennsylvania, Philadelphia, Pa.

[21] Appl. No.: 555,333

[22] Filed: Mar. 4, 1975

Related U.S. Application Data

[62] Division of Ser. No. 442,549, Feb. 14, 1974, abandoned, which is a division of Ser. No. 211,040, Dec. 22, 1971, Pat. No. 3,839,228, Ser. No. 114,061, Feb. 9, 1971, Pat. No. 3,803,256, Ser. No. 34,209, May 4, 1970, Pat. No. 3,706,814, Ser. No. 840,110, Jun. 16, 1969, abandoned, Ser. No. 830,687, Jun. 5, 1969, Pat. No. 3,655,813, Ser. No. 823,656, May 12, 1969, abandoned, Ser. No. 749,714, Aug. 2, 1968, abandoned, Ser. No. 716,190, Mar. 26, 1968, Pat. No. 3,865,884, Ser. No. 715,998, Mar. 26, 1968, Pat. No. 3,624,173, and Ser. No. 581,129, Aug. 25, 1966, abandoned.

[51] Int. Cl.$^3$ .............................................. C07C 2/58
[52] U.S. Cl. ................................. 585/722; 252/455 Z
[58] Field of Search ............... 260/683.43; 252/455 Z; 585/722

[56] References Cited

U.S. PATENT DOCUMENTS

| 3,251,902 | 5/1966 | Garwood et al. | 260/683.43 |
| 3,549,557 | 12/1970 | Bolton et al. | 260/683.43 |
| 3,795,714 | 3/1974 | Pickert et al. | 260/683.43 |
| 3,839,228 | 10/1974 | Kirsch et al. | 252/455 Z |
| 3,865,894 | 2/1975 | Kirsch et al. | 260/683.43 |

Primary Examiner—Curtis R. Davis
Attorney, Agent, or Firm—J. Edward Hess; Donald R. Johnson

[57] ABSTRACT

A hydrocarbon conversion catalyst composition, useful for paraffin-olefin alkylation, can comprise a three dimensional crystalline zeolite molecular sieve having a pore size large enough to adsorb 2,2,3-trimethylpentane and having a composition expressed in terms of mole ratios of oxides as $$a(I_2O):b(IIO):c(III_{2/3}O):d(IV_{1/2}O)Al_2O_3:eSiO_2$$

wherein I represents a monovalent metal cation; II represents a divalent metal cation; III represents a trivalent metal cation; IV represents a tetravalent cation; a has a value of from zero to 0.15; b has a value of from zero to 0.75; c and d each have values of from zero to 1; e has a value of from 2 to 20; with the proviso that when e has a value of from 2 to 3, the value of ((b+c)=0.75 to 1 and d=0; and with the proviso that when e has a value of > 3 to 4, the value of (b+c+d)=0.6 to 1.0; and with the further proviso that when e has a value of > 4 to 20, the value of (b+c+d)=0.25 to 1.0. In one embodiment said zeolite contains less than about 60 percent of its maximum OH exhibiting infrared absorption in the region of 3480 to 3670 cm.$^{-1}$; however in a slurry-reaction process the preferred catalysts have been activated at a temperature in the range of 400°–500° C. and contain about said maximum OH absorption. In the above catalyst, protons and/or ammoniumions can be present to preserve electronic equivalency. The degree of conversion of olefins and paraffins to saturated products can be increased by incorporation into the catalyst of a halide adjuvant containing bromine, chlorine or fluorine. One preferred catalyst can be represented, by the above formula as $$0.1(I_2O):0.7(III_{2/3}O):Al_2O_3:4.7SiO_2$$

where I is Na$^+$ and III is a trivalent rare earth metal, such as Ce$^{+3}$. More precisely, this catalyst can be represented as $0.1(Na_2O):0.2(H_2O):0.7(III_{2/3}O):Al_2O_3:4.7SiO_2$.

21 Claims, No Drawings

CRYSTALLINE ALUMINO-SILICATE ZEOLITES CONTAINING POLYVALENT METAL CATIONS

CROSS REFERENCES TO RELATED APPLICATIONS

This is a division of application Ser. No. 442,549, filed Feb. 14, 1974, now abandoned, which in turn is a divisional of Ser. No. 211,040, filed Dec. 22, 1971, now U.S. Pat. No. 3,839,228, which in turn is a continuation-in-part of all of the following copending applications, of the present inventors, Francis William Kirsch, David S. Barmby, and John D. Potts:

| Serial No. | Filing Date | Title |
| --- | --- | --- |
| 581,129 (Now abandoned) | 8-25-66 | Process for Paraffin-Olefin Alkylation |
| 715,998 (Now U.S. Pat. No. 3,624,173, issued 11-30-71) | 3-26-68 | Gd Zeolite and Hydrocarbon Conversion Process with Gd Zeolite Catalyst |
| 716,190 (Now U.S. Pat. No. 3,865,894) | 3-26-68 | Process for Paraffin Olefin Alkylation |
| 749,714 (Now Abandoned) | 8-2-68 | Dy Zeolite and Hydrocarbon Conversion Process with Dy Zeolite Catalyst |
| 823,656 (Now Abandoned) | 5-12-69 | Paraffin-Olefin Alkylate Composition |
| 830,687 (Now U.S. Pat. No. 3,655,813) | 6-5-69 | Continuous Alkylation Process |
| 840,110 (Now Abandoned) | 6-16-69 | Process for Producing Gasoline Blending Components |
| 34,209 (Now U.S. Pat. No. 3,706,814) | 5-4-70 | Continuous Process for Producing Gasoline Blanding Components |
| 114,061 (Now U.S. Pat. No. 3,803,256) | 2-9-71 | Process for Producing Gasoline Blending Components |

The disclosure of all of the above-cited copending applications is hereby incorporated in the present application.

In particular, paraffin and olefin feed components which can be converted to gasoline blending components by use of catalysts, of the present invention are disclosed in the above-cited copending applications. The said copending applications, (especially Ser. Nos. 581,129; 715,998 and 716,190) also disclose zeolites of the present invention, such as the substantially anhydrous acidic crystalline alumino-silicate zeolites which have a low alkali metal content and a high content of cations of a polyvalent metal.

The processes disclosed in the said patent applications for activation, hydration and regeneration of "aged" zeolite catalysts can also be useful means of improving the commercial utility of our zeolites, particularly for regeneration of "aged" catalysts which have been used to convert paraffin and olefin feed components to gasoline blending components.

In all of our previously cited applications (e.g., Ser. No. 581,129) we disclose a process for the production of highly saturated alkylate from monoolefins which requires not only a catalyst with a large number of acid sites of sufficient strength for hydride transfer but which also utilizes conditions which favor hydride transfer, such as introducing the olefin to the reactor in the liquid phase and in intimate admixture with $C_4-C_6$ isoparaffin and controlling the addition of said olefin such that the concentration of unreacted olefin in the reaction mixture is maintained at a low level.

In general, the preferred catalysts in this process are obtained from a polyvalent metal cation containing zeolite which is activated (as by heating) to remove most of its water content (and, if present, nitrogen compounds). Although in some of these applications a preferred catalyst, an activated Y zeolite having a high content of cations of CeIII, has been indicated by the symbol $Ce^{+3}Y$, the more precise symbol would be $Ce^{III}HNaY$, indicating that minor amounts of sodium can be retained in the zeolite and that electronic equivalency is maintained by "protonic" sites. Even more precision in catalyst definition can be provided by means of the formulas utilized herein (e.g., $0.1Na_2O:0.4-H_2O:0.5Ce_{\frac{2}{3}}O:Al_2O_3:4.5SiO_2$).

As is discussed in greater detail in copending application Ser. No. 716,190, it is sometimes advantageous to control the activation such that the activated catalyst contains about ¼ to 2 mole of "bound water" for each atom of exchanged polyvalent metal (e.g., in a cerium Y zeolite alkylation catalyst, in the range of 0.8–1.2 molecules of water will be evolved for each atom of cerium, upon ignition at 1800° F.). It can also be advantageous in some cases to control the activation so that the activated zeolite catalyst contains less than about 60 percent of its maximum OH exhibiting infrared absorption in the region of 3480–3670 cm$^{-1}$. This requirement can be fulfilled, for example, by utilizing the 600° F. activated catalysts described in our application Ser. No. 716,190.

BACKGROUND OF THE INVENTION

This invention relates to the production of normally liquid, saturated hydrocarbons, useful in gasoline blending, by reacting isoparaffins with olefins in liquid phase in the presence of a substantially anhydrous crystalline aluminosilicate zeolite, and to means of preparing such zeolites.

This application contains claims copied from U.S. Pat. No. 3,549,557 (Cl. 252-455) to Anthony P. Bolton and Paul E. Pickert, which issued December 33, 1970, on application Ser. No. 740,049, filed June 26, 1968. Said claims have also been presented (by amendment filed on Dec. 20, 1971) in our patent application Ser. No. 716,190 (which was filed Mar. 26, 1968).

In the prosecution of Ser. No. 740,049, the following patents were cited: U.S. Pat. No. 3,251,902 to Garwood et al, Cl. 260-683.64 U.S. Pat. No. 3,397,137 to Pickert et al, Cl 252-455X.

In U.S. Pat. No. 3,549,557, a zeolite which contained exchanged cations of polyvalent metals was defined as containing its maximum OH exhibiting infrared absorption in the region of 3480 to 3670 cm$^{-1}$, When "the thermally removable OH content of a given molecular sieve is fully developed (i.e., is at its maximum) . . . ". This maximum was further defined as being attained "when the zeolite has been heated to between 300° C. and 400° C.". This definition is used in the present application.

It was further stated that at least 40% of these OH can be thermally removed by heating the zeolite in the range off 550° C. to 800° C. For purposes of the present application, it is applicants' definition that this requirement for removal of at least 40% of these OH is met when the zeolite has lost 40 weight % of the "water" content at said maximum and that a zeolite which has been heated to 300° C., or higher, (572° F. contains no more than said maximum of these OH. Therefore, the requirement that a zeolite contain "less than about 60 percent of its maximum OH exhibiting infrared absorption in the region of 3480 to 3670 cm$^{-1}$ is defined herein as requiring that the zeolite has "total water", as determined by weight, loss on ignition (LOI), that is no more than 60% of the "total water" which the zeolite had after heating for 60 minutes at 300° C. In Table 4 hereof, (which is taken from our Ser. No. 716,190) the column headed "% max OH" is such a calculation made from the reported "total H$_2$O", obtained by ignition analysis.

Thus, Table 4 describes catalysts of the previously referred to chemical formulae and which, by definition, exhibit less than 40% (e.g. Run No. E-7) and less than 60% (Run No. E-9) of said maximum OH. These results are summarized below:

| Run No. | Temp. (°C.) | Total H$_2$O | % Max OH |
|---------|-------------|--------------|----------|
| E-4     | 300         | 0.216        | 100      |
| E-5     | 400         | 0.182        | 84       |
| E-6     | 500         | 0.157        | 77       |
| E-7     | 600         | 0.127        | 59       |
| E-8     | 700         | 0.116        | 54       |
| E-9     | 700         | 0.083        | 39       |

A zeolite similar in preparation to E-7, except that it had been activated for 2 hours at 600° C. (and an estimated LOI of about 2.5±0.2%), was used as the catalyst in the alkylation run in Example XIII (hereinafter) which produced 128.5% of C$_{5+}$ paraffin (based on olefin charged). Table 23 herein provides additional analytical data on this alkylation product.

A more precise correlation (or definition) of the maximum OH exhibiting infrared absorption in the region of 3480-3670 Cm$^{-1}$ is that this maximum corresponds to the value at 300° C. in the "H$_2$O for Ce" column of Table 4 herein. The requirement that a catalyst contain less than about 60 percent of said maximum is met when the "H$_2$O for Ce" has decreased by about 40% or more.

This correlation or definition can be seen in the following Table (taken from the Table 4 data):

| Run No. | Temp. (°C.) | H$_2$O for Ce | % Max OH |
|---------|-------------|---------------|----------|
| E-4     | 300         | 0.136         | 100      |
| E-5     | 400         | 0.102         | 75       |
| E-6     | 500         | 0.075         | 55       |
| E-7     | 600         | 0.046         | 34       |
| E-8     | 700         | 0.037         | 27       |
| E-9     | 700         | 0.007         | 5        |

SUMMARY OF THE INVENTION

A hydrocarbon conversion catalyst composition useful for paraffin-olefin alkylation, can comprise a three dimensional crystalline zeolite molecular sieve having a pore size large enough to adsorb 2,2,3-trimethylpentane and having a composition expressed in terms of mole ratios of oxides as $$a(I_2O):b(IIO):c(III_{\frac{2}{3}}O):d(IV_{\frac{1}{2}}O)Al_2O_3:eSiO_2$$

wherein I represents a monovalent metal cation; II represents a divalent metal cation; III represents a trivalent metal cation; IV represents a tetravalent cation; a has a value of from zero to 0.15; b has a value of from zero to 0.75; c and d each have values of from zero to 1; e has a value of from 2 to 20, with the proviso that when e has a value of from 2 to 3, the value of (b+c)=0.75 to 1 and d=0; and with the proviso that when e has a value of >3 to 4, the value of (b+c+d)=0.6 to 1.0; and with the further proviso that when e has a value of >4 to 20, the value of (b+c+d)=0.25 to 1.0. In one embodiment said zeolite contains less than about 60 percent of its maximum OH exhibiting infrared absorption in the region of 3480 to 3670 cm.$^{-1}$ (which can be achieved by activation at about 600° C. or higher); however in a slurry-reaction process the preferred catalysts contain about said maximum OH absorption and have been activated at a temperature in the range of about 400°-500° C. In the above catalyst protons and/or ammonium ions can be present to preserve electronic equivalency.

The degree of conversion of olefins and paraffins to saturated products can be increased by incorporation into the catalyst of a halide adjuvant containing bromine, chlorine or fluorine.

A preferred process for preparing a novel catalyst, useful for paraffin-olefin alkylation, is as follows:
(a) ammonium exchange of NaY zeolite until the resulting ammonium-exchanged zeolite contains less than 3% by weight of sodium;
(b) further exchanging the ammonium-exchanged zeolite with a solution comprising rare earth metal ions until the zeolite contains, on an ignited basis, at least 7% by weight of rare earth metal ions;
(c) heating the zeolite to a temperature in the range of 125°-300° C. until there is substantially no further loss of sorbed water, and
(d) subjecting the zeolite to a temperature in the range of 300°-700° C. (more preferred 320°-600° C.) in the presence of a gas or under reduced pressure until the desired OH adsorption is obtained, generally until substantially no further evolution of associated water occurs.

In one embodiment, in the catalyst composition of the above formula, the coefficient "a" can have a value of from zero to 0.08 and e can have a value of from 4 to 15.

In another embodiment, the zeolite can contain less than 40 percent of its maximum OH exhibiting infrared absorption in the region of 3480 to 3670 cm.$^{-1}$.

In another embodiment, when e has a value of >3 to 4, the value of (b+c+d)=0.6 to 0.85; and when e has a value >4 to 20, the value of (b+c+d)=0.45 to 0.75.

An especially valuable catalyst which can be prepared by this process comprises Ce, Gd or a mixture of Gd and Ce as the exchanged metal ions. One preferred catalyst can be represented by the above formula as $a(I_2O):c(III_{\frac{2}{3}}O);Al_2O_3:eSiO_2$ where a is about 0.1, I is Na, c is about 0.7, III consists essentially of rare earth metals and e is about 4.7 (the zeolite framework being Type Y).

FURTHER DESCRIPTION

This invention relates to crystalline alumino-silicate zeolites containing polyvalent metal cations (e.g., cations of cerium) and having a low content of monovalent metal cations (e.g., $Na^+$). Such zeolites, when "activated" can be useful for many hydrocarbon conversion reactions (e.g., alkylation, cracking, isomerization, hydroisomerization).

Our co-pending Application Ser. No. 716,190 relates to a process for the preparation of an olefin-paraffin alkylate comprising:

(a) contacting $C_3$-$C_6$ monoolefin in admixture with $C_4$-$C_6$ isoparaffin having a tertiary carbon atom, at a temperature below the critical temperature of the lowest boiling hydrocarbon reactant and at a pressure such that the reactants are in liquid phase, with a substantially anhydrous acidic crystalline aluminosilicate zeolite, and (b) stopping such contacting after substantial alkylation has occurred but before the weight rate of production of unsaturated hydrocarbon becomes greater than the weight rate of production of saturated hydrocarbon. The zeolites according to the present invention when activated, e.g., are in substantially anhydrous acidic form, and preferably when substantially free from nitrogen compounds, are particularly suitable for use in the above process.

Acidic crystalline alumino-silicate zeolites in hydrated form can in general be chemically characterized by the empirical formula $M_x(ALO_2)_x(SiO_2)_y(H_2O)_z$. Where M is $H^+$ and/or an equivalent valence of metal cations and x, y and z are integers, the ratio x/y being usually from 1.0 to 0.2, (although "acid-leached mordenites can be lower than 0.2, e.g., 0.1") A 10% aqueous suspension of an acidic zeolite will have a pH less than 7, preferably less than 5.

These acidic zeolites are normally prepared from alkali metal-containing zeolites (which in 10% aqueous solution will have a pH greater than 7, and usually greater than 9) by ion-exchanging the alkali metal ions for $H^+$ and/or polyvalent metal cations. Hydrocarbon-ion (or proton) exchange can be effected by exchange from aqueous or non-aqueous medium with mineral acids, such as dilute aqueous HCl, or by exchange with solutions of acids and polyvalent metal ions. Polyvalent metal exchange can be effected with solutions of salts of the metals, such as their nitrates. Alternatively the alkali metal-containing zeolite can be exchanged with a solution of an ammonium salt to form an ammonium zeolite which is converted to the acidic form by heating.

Prior to their use as catalysts the hydrous crystalline alumino-silicate zeolites are "activated". In general, this activation takes place by controlled heating under vacuum or in a stream of a gas, such as air, hydrogen, nitrogen, or oxygen, to remove water. In the case of ammonium-exchanged zeolites, not only water is removed but also the ammonium ion is decomposed to obtain a substantially anhydrous, "decationized" or "protonated" zeolite. Such zeolites are similar, in catalysis, to these prepared by direct exchange with an aqueous acid.

When the hydrous ammonium zeolite also contains polyvalent metal ions, the resulting activated zeolite will be partially protonated "or cation deficient". Such zeolites are not only highly acidic, but are more resistant to the detrimental effects of the activation procedure.

The heating rate and temperatures of such "activation" will depend to a great extent on the type of zeolite, especially the Al/Si atomic ratio, and the type and percent of polyvalent cations and monovalent ions such has hydrogen or ammonium ion. In any event the hydrated zeolite is first heated at a temperature sufficiently high to remove the bulk of the water from the pores of the zeolite. At atmospheric pressures this temperature is preferably from 125°-300° C.

In the case of an ammonium-exchanged zeolite the temperature is then raised to a higher temperature than that used for water removal and such temperature is maintained for a sufficient time to remove a substantial amount of the ammonium ion from the zeolite as $NH_3$. This removal also may involve decomposition of the ammonium ion by such reactions as oxidation of ammonia to nitrogen oxides or nitrogen and water.

At atmospheric pressure, with ammonium-exchanged zeolites which also contain appreciable quantities of exchanged polyvalent metal cations, this higher temperature is preferably 320°-500° C., but can be as high as 600° or 650° C. if care is taken to control the activation so as to retain at least 25% of the crystallinity of the zeolite.

Our copending application Ser. No. 716,190 compares alkylation with crystalline zeolite catalysts containing polyvalent metals and which were activated at various temperatures (e.g., 400°, 500° and 600° C.) and for varied periods of time. This data shows that these catalysts are all operative for alkylation. Analytical data is also presented which shows the reduction in OH groups (as residual $H_2O$) produced by such various activation procedures, particularly for temperatures in the range of 450°-1292° F.

With ammonium-exchanged zeolites which contain no polyvalent metal cations, it is important that the activation temperature be kept below about 400° C., since at higher temperatures the intensity of the X-ray diffraction peaks of the zeolite decreases greatly (due to a degradation of crystalline structure), and the resulting catalyst is less active for paraffin-olefin alkylation. In U.S. Pat. No. 3,130,007 a similar intensity measurement is used to determine the "percent zeolite", and appears to relate to crystallinity of the zeolite.

If an ammonium-exchanged crystalline alkali metal zeolite is further exchanged with polyvalent metal cations, the resulting polyvalent metal-$NH_4+$ exchanged zeolite retains a much greater proportion of its X-ray peak intensity after activation than does the base $NH_4+$-exchanged zeolite.

The present invention relates, for example, to crystalline zeolite Y containing at least one cation comprising cerium for every nine atoms of aluminium. When in acidic and substantially anhydrous form this zeolite has high alkylation activity when used as catalyst and retains a high degree of X-ray peak intensity on activation or regeneration. Preferred cerium containing cations are $Ce^{+3}$, $CeOH^{+3}$, $CeOH^{+2}$, $Ce(OH)_2^{+2}$ and $CeO^{+2}$.

As used herein the term "zeolite Y" is intended to mean the material defined in U.S. Pat. No. 3,130,007, which is marketed by the Union Carbide Corporation as "Linde Y".

The cerium containing zeolites of the present invention may be prepared by ion exchange in a solution containing cerium ions (preferably dilute, e.g. 0.1-6 wt% hydrated cerium III nitrate and preferably having a pH in the range of 4-6, more preferred 4.5±0.5).

In general, the concentration of the exchange solution should be no greater than that of a saturated solution at ambient temperature (e.g., about 65° F.). Although, exchange at an elevated temperature below boiling (e.g., 80° C.) is preferred, a solution of greater concentration than saturated at ambient temperature can lead to occlusion of precipitated salt (due to cooling during the filtration step.)

Similarly, a pH above about 6.0 can lead to hydroxide precipitation and a pH below about 4.0 can lead to destruction of crystallinity.

A preferred process for preparing a substantially anhydrous acidic crystalline zeolite Y containing polyvalent metal cation (e.g., comprising cations of cerium) comprises:

(a) ammonium ion exchange of crystalline sodium Y zeolite until the resulting ammonium-exchanged Y zeolite contains on an ignited basis, no more than 3% by weight sodium (more preferred, no more than about 10% of the exchange capacity of the zeolite should be satisfied by $Na^+$);

(b) further exchanging the ammonium-exchanged zeolite with a solution containing cations of a polyvalent metal (e.g., cerium ions), until the zeolite contains, on an ignited basis, a high polyvalent metal cation content (e.g., at least 7% by weight of cerium, (preferably, at least 40% (more preferred 60–80%) of the exchange capacity should be satisfied by such cations.

(c) heating the zeolite to a temperature in the range of about 125°–300° C. until there is substantially no further weight loss; and (d) subjecting the zeolite to a temperature in the range of (320°–700° C., more preferred 320°–500° C.) in the presence of a gas until substantially no further evolution of ammonia occurs.

For example, the ammonium exchanged zeolite Y is further exchanged with an aqueous solution of cerium nitrate (pH about 4.0–4.5).

ILLUSTRATIVE EXAMPLES

The present invention may be further illustrated by the following specific examples. Examples I–VI illustrate the preparation of acidic, or potentially acidic, solvated crystalline zeolites by aqueous cation exchange. Example VII illustrates the "activation" of the solvated zeolites by removing "solvent" from the zeolite.

The remaining examples, illustrate the use of such substantially anhydrous acidic crystalline alumino-silicate zeolites as alkylation catalysts. Of these, Examples VIII–XII show the effect of reaction temperature on the yield and product distribution. Examples X, XI and XII show the unexpected, large increase in product yield effected by the use of various halide adjuvants.

Example XIII illustrates the effect of the gas used in catalyst activation on the paraffin yield, per weight of olefin charged, obtained from the resulting catalyst.

Example XIV illustrates the correlation between alkylate yield and the ESR measurements of total spin count when aromatic hydrocarbons are adsorbed on the CeHY catalyst.

Example XV illustrates the effect that catalyst composition can have on yield and product distribution in alkylation.

In the Examples which report a catalyst analysis, such data can be used to calculate the coefficients in the previously referred to empirical zeolite formulae. Such coefficients for the formula

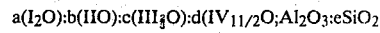
$$a(I_2O):b(IIO):c(III_{\frac{2}{3}}O):d(IV_{11/2}O;Al_2O_3:eSiO_2$$

are reported below for certain zeolites of the examples (along with certain necessary additional coefficients). The above formula omits the content of non-metal cations ($H^+$, $NH_4^+$) in the zeolite. A more precise formula for an $NaNH_4HCeY$ zeolite is:

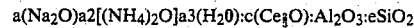
$$a(Na_2O)a2[(NH_4)_2O]a3(H_2O):c(Ce_{\frac{2}{3}}O):Al_2O_3:eSiO_2$$

These coefficients are reported below:

| Sample No. | a | a2 | a3* | c | e |
|---|---|---|---|---|---|
| E1 | 0.0876 | 0.1208 | 0.1087 | 0.6823 | 4.70 |
| E5 | 0.0971 | 0.1161 | 0.0898 | 0.6966 | |
| E7 | 0.1018 | 0.0213 | 0.1774 | 0.6966 | |
| E8 | 0.1066 | 0.0213 | 0.1585 | 0.7107 | |
| E9 | 0.0805 | 0.0213 | 0.1940 | 0.7035 | |
| C6 | 0.0853 | 0.0331 | 0.1822 | 0.6966 | |
| D6 | 0.0897 | 0.0968 | 0.1136 | 0.7017 | |

*corresponds to $H^+$ derived from deficiency in ion-summation and representated as "$H_2O$". Runs E7, E8 and E9 showed a positive nitrogen content of less than 0.1 weight % (the limit for the analytical method).

Note that in these zeolites the coefficient a is about 0.1, c is about 0.7, e is about 4.7 and the sum of a2+a3 is about 0.2, corresponding to about $0.1(I_2O):0.7(III_{\frac{2}{3}}O):Al_2O_3:4.7SiO_2$, for the less precise general formula. A more precise expression could be $0.3(I'_2O):0.7(III_{\frac{2}{3}}):Al_2O_3:4.7SiO_2$ where the "a" coefficient also includes a2 and a3 for the non-metal monovalent cations.

Another means of reporting zeolite composition (e.g., see U.S. Pat. No. 3,236,762) is to calculate the "cation distribution", based on elemental analysis of the zeolite (and assuming that electronic balance is preserved by "protons" or "$H^+$", which are, thus, calculated by difference).

The following table reports such cation distribution for certain zeolites of the examples (where $M^{+n}$ represents the cations of polyvalent metals, e.g., $Ce^{+3}$):

| Ex. No. | Analysis % Na | % N | "As Is"* % $M^{+n}$ | Basis % LoI | % Cation Distribution | | | |
|---|---|---|---|---|---|---|---|---|
| | | | | | $Na^+$ | $NH_4^+$ | $H^+$ | $Ce^{+3}$ |
| I | 1.34 | 4.6 | | 26.5 | 18.5 | 81.5 | | |
| I | 5.5 | 2.3 | | 25.6 | 75.1 | 24.9 | | |
| II | 0.77 | 4.14 | | 29.8 | 11.2 | 88.8 | | |
| II | 0.21 | 4.64 | | 28.7 | 3.1 | 96.9 | | |
| IV | 0.69 | 0.68 | 10.1 | 24.4 | 9.4 | 15.3 | 7.0 | 68.3 |
| IV | 0.23 | 0.8 | 10.3 | 24.7 | 3.2 | 18.0 | 9.4 | 69.6 |
| V | 1.69 | | 9.6 | 25.1 | 22.9 | | 13.2 | 63.9 |
| VI | 0.63 | | 7.7 | 26.4 | 9.0 | | 36.7 | 54.3 |
| VI | 0.22 | 2.8 | 5.3 | 27.6 | 3.0 | 48.2** | | −48.8 |
| VI | 1.3 | 0.26 | 9.9 | 22.5 | 16.9 | 19.4 | | 63.7 |

*"As Is" basis is, generally, for the "dried" zeolite after equilibration in a dessicator over a sodium chloride-water solution
**Calculated by difference since nitrogen analysis appears to be high, perhaps due to occluded ammonium salts).

For convenience, the cation distributions in the above table can be rounded off to whole numbers and reported in the following manner:

| Example | As Is | After Activation* |
|---|---|---|
| I | 18Na 82$NH_4$ | 18Na 82H |
| I | 75Na 25$NH_4$ | 75N 25H |
| II | 11Na 89$NH_4$ | 11N 89H |

-continued

| Example | As Is | After Activation* |
|---------|-------|-------------------|
| II | 3Na 97NH$_4$ | 3Na 97H |
| IV | 9Na 15NH$_4$ 7H 68Ce | 9Na 23H 68Ce |
| IV | 3Na 18NH$_4$ 10H 69Ce | 3Na 28H 69Ce |
| V | 23Na 13H 64Ce | 23Na 13H 64Ce |
| VI | 9Na 37H 54Ce | 9Na 37H 54Ce |
| VI | 3Na 48NH$_4$ 49Ce | 3Na 48H 49Ce |
| VI | 17Na 19NH$_4$ 64Ce | 17Na 19H 64Ce |

EXAMPLE I

This example describes the ammonium exchange of a crystalline, alkali metal alumino-silicate zeolite which can be heated to remove "loosely bound" water and to decompose the ammonium ion to produce a substantially anhydrous acidic crystalline alumino-silicate zeolite which can be used as a catalyst in our process. Preferably, before such decomposition or "decationizing", such ammonium-exchanged zeolites are further exchanged with polyvalent metal cations, as is shown in Example III hereinafter.

A kilogram of a commercially available hydrated crystalline alumino-silicate zeolite, identified as sodium zeolite Y, was dried in air at 125° C. for 18 hrs., broken up into particles of 100 mesh or less, redried in air at 125° C. for 18 hrs., and suspended with stirring, in 1.7 liters of a 9.1% by weight aqueous solution of ammonium chloride at 80° C. After 30 minutes the resulting ammonium-exchanged Y zeolite was separated from the liquid by filtration and recontacted at 80° C. in a similar manner with a second 1.7 liter portion of fresh NH$_4$Cl solution. After 6 more such 30-minute exchange cycles, the filtered zeolite was washed with distilled water (pH 6.5) at 20° C. until no chloride ion could be detected in the spent wash liquid with acidic silver nitrate reagent.

The washed ammonium-exchanged zeolite was dried for about 18 hours in air at 125° C., then ground to about 200 mesh and stored. The dried ammonium-exchanged zeolite produced by the above series of eight ammonium exchanges analyzed 1.34% Na and 4.6% N, and had a loss on ignition of 26.5%. After the first ammonium-exchange cycle, a similarly washed and dried portion of the zeolite analyzed 5.5% Na and 2.3% N, and had a loss on ignition of 25.6%.

The sodium Y zeolite before this ammonium exchange had a pore size sufficiently large to enable it to absorb benzene and analyzed 7.5% sodium and 8.86% aluminum, and had an Al/Si atomic ratio of 0.40. The sieve had a loss on ignition at 1800° F. of 23.8%. All ignition losses referred to hereinafter were run at 1800° F.

EXAMPLE II

This example illustrates the preparation of more highly ammonium-exchanged zeolites than that of Example I. Example I was repeated except that the sodium Y zeolite was subjected to 8 additional hot NH$_4$Cl exchange cycles before it was washed chloride free. The washed, dried ammonium-exchanged zeolite, resulting from this total of 16 ammonium-exchange cycles, contained 0.77% sodium and 4.14% nitrogen, and had 29.8% loss on ignition.

A similar exchange for a total of 32 cycles produced a washed, dried zeolite containing 0.21% Na and 4.64% N and having 28.7% loss on ignition.

Ammonium exchange of alkali metal zeolites can also be accomplished by suspending the zeolite in a vessel containing the exchange solution and maintaining a flow of fresh exchange solution into the vessel while withdrawing an equal volume of catalyst-free liquid from the vessel. Removal of catalyst-free liquid from the vessel can be effected by forcing the liquid with pressure or suction through a pleated microporous, woven stainless steel screen "10 micron" filter. In such continuous flow processing, the flow rate is preferably regulated so as to maintain a relatively constant pH in the exchange vessel. Hydrochloric acid or nitric acid addition can also be used for pH control. With 10% ammonium chloride solutions it is preferred to maintain a pH of about 4.5±0.3 (at 80° C.). Ammonium exchange can also be effected by percolating the exchange solution through a fixed bed of zeolite.

EXAMPLE III

This example illustrates the further exchange of an ammonium-exchanged zeolite with a solution containing polyvalent metal ions in order to produce a zeolite containing both polyvalent metal ions and ammonium ions. A portion of the dried, ammonium-exchanged zeolite of Example I was contacted, with stirring, for 30 minutes at 80° C. with 1.7 parts by weight of a 1.3% solution of Ce(NO$_3$)$_3$.6H$_2$O, then separated from the exchange solution by filtration and recontacted for 30 minutes at 80° C. with 1.7 parts by weight of fresh cerium nitrate solution. After 6 more such exchange cycles (or a total of 8 exchanges), the filtered Ce$^{+3}$-exchanged/ammonium-exchanged zeolite was washed with water until no nitrate ion could be detected in the spent liquor by diphenylamine reagent. The washed Ce-NH$_4$+Y zeolite was dried for 18 hours at 125° C., ground, redried for 18 hours at 125° C., and stored in a moisture-tight container. The dried Ce$^{+3}$-NH$_4$$^+$-exchanged zeolite analyzed 6.18% Ce, 1.25% Na, and 1.43% N. It had a 25.6% weight loss on ignition.

EXAMPLE IV

This example illustrates the use of additional cerium-exchange cycles and a more highly ammonium-exchanged "base" zeolite in order to obtain zeolites with a greater cerium content and a lower sodium content than the zeolite of Example III. A portion of the washed, dried "16 cycle" NH$_4$$^+$-exchanged zeolite of Example II was contacted according to the procedure of Example III for a total of 16 Ce(NO$_3$)$_3$ exchange cycles, then similarly washed and dried. The resulting Ce$^{+3}$-NH$_4$$^+$-exchanged zeolite analyzed 10.1% Ce, 0.69% N, 0.68% Na, and had a loss on ignition of 24.4%.

A similar series of 16 cerium exchanges performed on the "32 cycle" ammonium-exchanged zeolite of Example II produced a washed, dried Ce$^{+3}$-NH$_4$$^+$-exchanged zeolite which analyzed 0.23% Na, 10.3% Ce, 0.8% N, and had a loss on ignition of 24.7%.

Hereinafter, sometimes, a catalyst will be identified according to the number and type of such exchange cycles according to the code: number of ammonium exchange cycles/number of polyvalent metal exchange cycles. That is, the above zeolite prepared by 6 cerium exchange cycles of a 32 cycle ammonium is, by this code, a 32/16 zeolite, (or, after activation, a 32/16 catalyst).

EXAMPLE V

This example illustrates the preparation of a Ce$^{+3}$-exchanged sodium Y zeolite. A portion of the commercial sodium Y zeolite of Example I was ground and exchanged for 16 exchange cycles with Ce(NO$_3$)$_3$ solution in a manner similar to the exchange of Example III, then washed and dried. The resulting Ce$^{+3}$-exchanged Na Y zeolite contained 9.6% certium, 1.69% sodium, and had a loss on ignition of 25.1%.

The cerium exchanges of Examples III, IV and this example can be effected in a continuous manner, similar to that described in Example II for ammonium exchanges. Preferably the pH should be about 4.5. The particular polyvalent metal salt chosen and the pH of the exchange solution will determine whether the cationic exchange species is the metal or a hydroxylated complex ion of the metal. Other polyvalent metal ions, such as those referred to hereinafter, and in particular cations of the polyvalent rare earth metals and mixtures thereof, may be similarly exchanged with alkali metal-containing and/or ammoniumcontaining crystalline zeolites. Especially preferred catalysts can be obtained from crystalline alumino-silicate zeolites which have been so exchanged with aqueous solutions of salts of gadolinium, such as Gd(NO$_3$)$_3$, or with mixtures of salts of Gd and Ce. In this specification, the term "rare earth metals" includes lanthanum, that is, the term "rare earth" herein is used as a synonym for "lanthanon". The lanthanons include La, Ce, Pr, Nd, Sm, Eu, Gd, Tb, Dy, Ho, Er, Tm, Yb and Lu.

EXAMPLE VI

This example illustrates the ammonium exchange of a Ce$^{+3}$-exchanged sodium Y zeolite. A portion of a washed, dried cerium-exchanged zeolite prepared similar to that of Example V and containing 7.7% Ce, 0.63% Na and with 26.4% loss on ignition was exchanged with hot aqueous ammonium chloride, for a total of 8 cycles, using the procedure of Example I. The washed, dried NH$_4$$^{+}$-$^{Ce+3}$-exchanged Y zeolite analyzed 0.22% Na, 2.8 N, 5.3 Ce$^{+3}$ and had a loss on ignition of 27.6%. Therefore, about 30% of the cerium was removed from the cerium-exchanged Na Y zeolite during the ammonium-exchange cycle.

An alkali metal zeolite which was exchanged by the reverse procedure, that is, 8 ammonium exchanges followed by 16 cerium exchanges, contained 87% more cerium (it analyzed 9.9% Ce, 1.3% Na and 0.26% N, and had a loss on ignition of 22.5%).

EXAMPLE VII

This example illustrates a preferred method of "activation" of hydrous crystalline alumino-silicate zeolites prior to their use as catalysts in our paraffin-olefin alkylation process. In general, hydrous crystalline zeolites are activated by controlled heating under vacuum or in a stream of a gas, such as air, hydrogen, nitrogen, helium or oxygen, to remove water. In the case of ammonium-exchanged zeolites, not only is loosely bound water removed but also the ammonium ion is decomposed to obtain a substantially anhydrous, "decationized" or "protonated" zeolite. Such zeolites are highly acidic and are similar catalytically to those prepared by direct exchange with an aqueous acid.

When the hydrous ammonium zeolite also contains polyvalent metal ions, the resulting activated zeolite will be partially protonated or "cation deficient". Such zeolites are not only highly acidic, but are more resistant to the detrimental effects of the activation procedure.

The heating rate and temperatures of such "activation" will depend to a great extent on the type of zeolite, that is, the Al/Si atomic ratio, and the type and percent of polyvalent cations and monovalent ions such as hydrogen or ammonium ion. In any event the hydrated zeolite is first heated at a temperature sufficiently high to remove the bulk of the "uncombined" or "uncomplexed" water from the pores of the zeolite. At atmospheric pressures this temperature is preferably from 125°–300° C., most preferably from 125°–240° C.

In the case of an ammonium-exchanged zeolite the temperature is then raised to a higher temperature than that used for such water removal and such temperature is maintained for a sufficient time to remove a substantial amount of the ammonium ion from the zeolite as NH$_3$. This removal may also involve decomposition of the ammonium ion by such reactions as oxidation of ammonia to nitrogen oxides or nitrogen and water.

At atmospheric pressure, with ammonium-exchanged zeolites which also contain appreciable quantities of exchanged polyvalent metal cations, this higher temperature is preferably 320–500° C.

With ammonium-exchanged zeolites which contain no polyvalent metal cations or have a low content of polyvalent cations, it is important that the activation temperature be kept below about 400° C., since at higher temperatures the intensity of the X-ray diffraction peaks of the zeolite decreases greatly (due to a degradation of crystalline structure) and the resulting catalyst is less active for paraffin-olefin alkylation. In U.S. Pat. No. 3,130,007 a similar intensity measurement is used to determine the "percent zeolite", and appears to relate to crystallinity of the zeolite.

We have also found that, if an ammonium-exchanged crystalline alkali metal zeolite is further exchanged with polyvalent metal cations, the resulting polyvalent metal NH$_4$$^{+}$-exchanged zeolite retains a much greater proportion of its X-ray peak intensity after activation than does the base NH$_4$$^{+}$-exchanged zeolite. Although small quantities of polyvalent cations will be of some benefit in this respect, for our catalysts it is preferable that the zeolite contain at least the following quantity of polyvalent metal cations (or a combination thereof of equivalent valence):

(1) at least one tetravalent metal, metal oxide or metal hydroxide for every 16 atoms of aluminum in the alumino-silicate tetrahedra of the zeolite, or (2) at least one trivalent metal, metal oxide or metal hydroxide for every 12 atoms of aluminum in the alumino-silicate tetrahedra, or (3) at least one divalent metal, metal oxide or metal hydroxide for every 8 atoms of aluminum in the alumino-silicate tetrahedra.

In addition, for optimum activity, the polyvalent cation should be selected from classes 1, 2 and 3 above (and mixtures thereof) when the atomic ratio Al/Si of the aluminosilicate tetrahedra comprising the zeolite is greater than 0.65, or from classes 2 and 3 above (and mixtures thereof) when the atomic ratio Al/Si is from 0.65 to 0.35, or from class 3 above when the atomic ratio Al/Si is less than 0.35. For example, the cation of our zeolite catalyst is preferably selected from the following:

(1) at least one cation selected from the class consisting of V$^{+4}$, Mo$^{+4}$, W$^{+4}$, Pa$^{+4}$, U$^{+4}$, VOH$^{+4}$, Cr(OH)$_2$$^{+4}$, CrO$^{+4}$, MnO$^{+4}$, Mn(OH)$^{+4}$, NbOH$^{+4}$, MoOH$^{+4}$, Mo(OH)$_2$$^{+4}$, NoO$^{+4}$, RuO$_2$$^{+4}$, Ru(OH)$_4$$^{+4}$, RuO$^{+4}$, Ru(OH)$_2$$^{+4}$, $SbOH^{+4}$, $OW^{+4}$, $W(OH)_2^{+4}$, $WOH^{+4}$, $Re(OH)_3^{+4}$, $Re(OH)_2^{+4}$, $ReO^{+4}$, $Os(OH)_4^{+4}$, $OsO_2^{+4}$, $OOs^{+4}$, $Os(OH)_2^{+4}$, $IrO^{+4}$, $Ir(OH)_2^{+4}$, $BiOH^{+4}$, $PaOH^{+4}$, $UO^{+4}$, $U(OH)_2^{+4}$, and $UOH^{+4}$, when Al/Si is from 1.0 to 0.65, (2) at least one cation selected from the group consisting of $Al^{+3}$, $Ni^{+3}$, $Ti^{+3}$, $TiOH^{+3}$, $V^{+3}$, $VOH^{+3}$, $VO^{+3}$, $V(OH)_2^{+3}$, $Cr(OH)_3^{+3}$, $Mn(OH)_4^{+3}$, $MnO_2^{+3}$, $Mn(OH)_3^{+3}$, $Mn(OH)^{+3}$, $Mn^3$, $GeOH^{+3}$, $ZrOH^{+3}$, $Nb(OH)_2^{+3}$, $NbO^{+3}$, $Mo(OH)_3^{+3}$, $Mo(OH)_2^{+3}$, $MoO^3$, $MoOH^{+3}$, $Mo^{+3}$, $Ru^{+3}$, $RuOH^{+3}$, $Ru(OH)_3^{+3}$, $Ru(OH)_5^{+3}$, $Rh^{+3}$, $RhOH^{+3}$, $PdOH^{+3}$, $SnOH^{+3}$, $Sb^{+3}$, $Sb(OH)_2^{+3}$, $SbO^{+3}$, $La^{+3}$, $HfOH^{+3}$, $Ta(OH)_2^{+3}$, $TaO^{+3}$, $W(OH)_3$, $WO^{+3}$, $W(OH)_2^{+3}$, $WOH^{+3}$, $W^{+3}$, $Re(OH)_4^{+3}$, $ReO_2^{+3}$, $Re(OH)_3^{+3}$, $ReOH^{+3}$, $Os^{+3}$, $OsOH^{+3}$, $Os(OH)_3^{+3}$, $Os(OH)_5^{+3}$, $Ir^{+3}$, $IrOH^{+3}$, $Ir(OH)_3^{+3}$, $PtOH^{+3}$, $PbOH^{+3}$, $Bi^{+3}$, $Bi(OH)_2^{+3}$, $BiO^{+3}$, $PoOH^{+3}$, $Ce^{+3}$, $CeOH^{+3}$, $Pr^{+3}$, $PrOH^{+3}$, $Sm^{+3}$, $Gd^{+3}$, $Tb^{+3}$, $TbOH^{+3}$, $Dy^{+3}$, $ThOH^{+3}$, $PaO^{+3}$, $Pa(OH)_2^{+3}$, $PaOH^{+3}$, $U(OH)_3^{+3}$, $U(OH)_2^{+3}$, $UO^{+3}$, $UOH^{+3}$, $U^{+3}$, when Al/Si is from 0.65 to 0.35, and (3) at least one cation selected from the class consisting of $Mg^{+2}$, $Ca^{+2}$, $Ba^{+2}$, $Sr^{+2}$, $ScOH^{+2}$, $TiO^{+2}$, $Ti(OH)_2^{+2}$, $TiOH^{+2}$, $V(OH)_3^{+2}$, $V(OH)_2^{+2}$, $VO^{+2}$, $VOH^{+2}$, $V^{+2}$, $Cr(OH)_4^{+2}$, $CrO_2^{+2}$, $CrOH^{+2}$, $Cr^{+2}$, $Mn(OH)_5^{+2}$, $Mn(OH)_4^{+2}$, $MnO_2^{+2}$, $Mn(OH)_2^{+2}$, $MnO^{+2}$, $Mn^{+2}$, $MnOH^{+2}$, $Fe^{+2}$, $FeOH^{+2}$, $Co^{+2}$, $CoOH^{+2}$, $Ni^{+2}$, $NiOH^{+2}$, $GaOH^{+2}$, $Ge(OH)_2^{+2}$, $GeO^{+2}$, $YOH^{+2}$, $Zr(OH)_2^{+2}$, $ZrO^{+2}$, $Nb(OH)_3^{+2}$, $NbOH^{+2}$, $Mo(OH)_4^{+2}$, $MoO_2^{+2}$, $Mo(OH)_3^{+2}$, $Mo(OH)_2^{+2}$, $MoO^{+2}$, $MoOH^{+2}$, $Mo^{+2}$, $Ru^{+2}$, $RuOH^{+2}$, $Ru(OH)_2^{+2}$, $RuO^{+2}$, $Ru(OH)_4^{+2}$, $Ru(OH)_6^{+2}$, $RuO_3^{+2}$, $Rh^{+2}$, $RhOH^{+2}$, $Rh(OH)_2^{+2}$, $RhO^{+2}$, $Pd^{+2}$, $Pd(OH)_2^{+2}$, $InOH^{+2}$, $RuO_2^{+2}$, $Sn(OH)_2^{+2}$, $SnO^{+2}$, $Sn^{+2}$, $SbOH^{+2}$, $Sb(OH)_3^{+2}$, $LaOH^{+2}$, $Hf(OH)_2^{+2}$, $HfO^{+2}$, $Ta(OH)_3^{+2}$, $W(OH)_4^{+2}$, $WO_2^{+2}$, $W(OH)_3^{+2}$, $W(OH)_2^{+2}$, $WO^{+2}$, $WOH^{+2}$, $W^{+2}$, $Re(OH)_5^{+2}$, $Re(OH)_4^{+2}$, $ReO_2^{+2}$, $Re(OH)_2^{+2}$, $ReO^{+2}$, $Re^{+2}$, $Os^{+2}$, $OsOH^{+2}$, $Os(OH)_2^{+2}$, $OsO^{+2}$, $Os(OH)_4^{+2}$, $OsO_2^{+2}$, $Os(OH)_6^{+2}$, $OsO_3^{+2}$, $Ir^{+2}$, $IrOH^{+2}$, $Ir(OH)_2^{+2}$, $IrO^{+2}$, $Ir(OH)_4^{+2}$, $IrO_2^{+2}$, $Pt^{+2}$, $PtO^{+2}$, $AuOH^{+2}$, $TlOH^{+2}$, $Pb(OH)_2^{+2}$, $PbO^{+2}$, $Pb^{+2}$, $BiOH^{+2}$, $Bi(OH)_3^{+2}$, $Po(OH)_2^{+2}$, $PoO^{+2}$, $Po^{+2}$, $AcOH^{+2}$, $CeOH^{+2}$, $Ce(OH)_2^{+2}$, $CeO^{+2}$, $PrOH^{+2}$, $Pr(OH)_2^{+2}$, $PrO^{+2}$, $NdOH^{+2}$, $Eu^{+2}$, $PmOH^{+2}$, $SmOH^{+2}$, $Sm^{+2}$, $EuOH^{+2}$, $Gd^{+2}$, $GdOH^{+2}$, $TbOH^{+2}$, $Tb(OH)_2^{+2}$, $Dy^{+2}$, $DyOH^{+2}$, $HoOH^{+2}$, $ErOH^{+2}$, $TmOH^{+2}$, $Tm^{+2}$, $YbOH^{+2}$, $Yb^{+2}$, $LuOH^{+2}$, $Th(OH)_2^{+2}$, $ThO^{+2}$, $Pa(OH)_3^{+2}$, $Pa(OH)_2^{+2}$, $PaO^{+2}$, $U(OH)_4^{+2}$, $UO_2^{+2}$, $U(OH)_3^{+2}$, $UO^{+2}$, $U(OH)_2^{+2}$, $UOH^{+2}$, when Al/Si is less than 0.35.

Thomsonite, levynite, and the Type X zeolite of U.S. Pat. No. 2,822,244 are crystalline zeolites having an Al/Si atomic ratio greater than 0.65. Analcite, chabazite, phillipsite, and the Type Y zeolite of U.S. Pat. No. 3,130,007 have Al/Si ratios between 0.65 and 0.35. Heulandite and the Type L zeolite of U.S. Pat. No. 3,013,984 have Al/Si ratios less than 0.35. Mordenite has an Al/Si ratio in the range of 0.2 and some mordenites have been reported to have an Al/Si ratio appreciably less than 0.2 (e.g., 0.13). Such low Al content mordenites, when exchanged and activated by the procedures taught herein, have some catalytic activity in our process but are not among our preferred catalysts.

As catalysts in our process we further prefer substantially anhydrous protonated alumino-silicates which are capable of adsorbing benzene, wherein the ratio Al/Si in the tetrahedra is from 0.65 to 0.35 and which contain at least one rare earth metal cation for every 9 aluminum atoms in the tetrahedra since such catalysts have high alkylation activity and retain a high degree of X-ray peak intensity on activation or regeneration.

For example, in illustration of our preferred method of activation of a preferred species of hydrous zeolite, the 16-cycle $Ce^{+3}$-exchanged/16-cycle $NH_4$-exchanged zeolite of Example IV was heated at 230° C. in a rotating kiln in a stream of flowing air for about one hour to remove water. No loss of ammonium ions was detected during this heating period. The temperature of the kiln was then raised at the rate of about 10° C. per minute to a temperature of 400° C. During this heating, ammonia could be detected, by $MnSO_4$-$AgNO_3$ reagent, in the exhaust gases from the kiln. The kiln was maintained at 400° C. for 2 hours, at which point no ammonia could be detected in the exhaust gases. The heat was then removed from the kiln and the kiln was cooled rapidly in a flowing stream of dry air. The activated catalyst was maintained overnight in a slowly flowing stream of dry air. The resulting, substantially anhydrous, protonated crystalline alumino-silicate had a loss on ignition of 3.7%.

Summation of the intensity of the significant X-ray diffraction peaks of the hydrous zeolite before activation and of an activated sample showed no decrease in intensity for the activated zeolite. In contrast, a similarly activated portion of the base 16-cycle ammonium-exchanged zeolite showed an intensity decrease of 64%.

To illustrate the stabilizing effect of even small quantities of polyvalent metal ions, a samle of the base 16-cycle ammonium-exchanged zeolite was submitted to a 16-cycle $Ce^{+3}$ exchange using 1/10 the usual cerium salt concentration to produce a dried, washed zeolite which analyzed 1.23% Ce (ignited basis). After activation according to the above procedure, the activated zeolite showed an intensity decrease of 47.4%.

The bulk density in g/ml of the "dry" (at 125° C.) hydrated zeolite is about 0.71 for sodium Y zeolite, 0.78 for highly ammonium-exchanged sodium Y zeolite ($NH_4Y$), 0.90 for highly cerium-exchanged $NH_4Y$ ($CeNH_4Y$) and 0.89 for highly Gdexchanged $NH_4Y$ ($GdNH_4Y$). If one assumes no significant volume change in activation, the calculated bulk density of the corresponding activated or substantially anhydrous zeolite would be in the range of 0.6 g/ml for the NaY and 0.75 g/ml for the CeHY.

Quantitative studies of the activation of "equilibrated" higly ammonium-exchanged sodium Y zeolite (hereinafter, sometimes $NH_4Y$) and cerium exchanged, $NH_4Y$ (hereinafter, sometimes $CeNH_4Y$) have shown that, in our preferred catalysts, even after our optimum activation, water can be evolved from the catalyst upon ignition at 1800° F. This water is called hereinafter sometimes, "bound", or "combined" or "complexed" water to distinguish it from that water which is readily evolved from the exchanged zeolite below 300° C. Equilibrated zeolite is a zeolite which has been exposed to air of about 50% relative humidity, at about 60° C. for about 12 hours.

We have further established that our preferred substantially anhydrous, acidic crystalline zeolite catalyst, containing polyvalent metal ions and, more preferably, having some degree of protonation, sometimes termed "cation deficiency", will evolve substantially no bound water when heated for about one hour at 300° C. but when ignited at 1800° F. will evolve about ¼ to 2 mole of water for each atom of exchanged polyvalent metal. In particular, in our novel, activated, cerium-containing catalysts, for each atom of cerium in the catalyst, 0.8 to 1.2 molecules of water will be evolved upon ignition at 1800° F.

We have concluded that in the catalyst this water is present, mainly, in the form $Ce(OH)^{2+}$. To understand the basis for this finding, one must first consider the behavior on activation of the hydrated NaY and $NH_4Y$ zeolites. Behavior of $NH_4Y$ catalyst during activation at temperatures from 150° to 1292° F. (65° to 700° C.) and for times up to 4 hours, is as summarized in Table 1. Two series of experiments were performed. Experiment A being at different times at constant temperature and Experiment B being at different temperatures at constant time. Total water (that is, sorbed and combined) appeared to be retained by this catalyst more firmly than ammonia.

Table 1 shows that about two-thirds of the total water present on "dried" $NH_4Y$ zeolite had been removed after one hour at 450° F. This water removal is an endothermic reaction and probably represents "loosely" held water that is in molecular form when sorbed. Data from DTA-EGA measurements agree with this observation.

Water removable only at 750° F. and higher temperatures is more firmly bound and is chemically combined in a form other than molecular $H_2O$. Ammonia, which is largely in the form of $NH_4^+$ ions, was removed more readily than the water which remains after one hour at 450° F. Furthermore, ammonia removal releases protons ($NH_4^+ \rightarrow NH_3 + H^+$). When an activated $NH_4Y$ zeolite is ignited at 1800° F., OH groups are destroyed and $H_2O$ is evolved in an amount equivalent to one molecule of $H_2O$ for every two OH groups.

Uytterhoeven, Christner and Hall, *J. PHYS. CHEM.*, 69, 2117-26 (1965), have proposed the following stoichiometry to account for protonation and dehydroxylation:

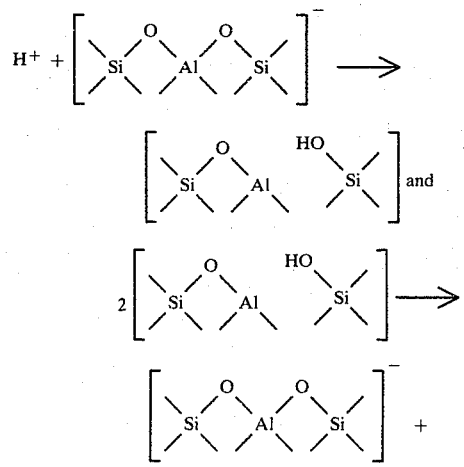

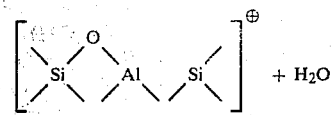

In an analogous manner, residual $NH_4^+$ ions can be expected to undergo similar changes when an activated zeolite is ignited at 1800° F. Therefore, whether $NH_4^+$ groups are intact or have been deaminated, one $H_2O$ should be detected upon ignition of activated catalyst for every two $NH_4^+$ ions originally in the zeolite.

Comparing $H_2O$ contents of activated $NH_4^+$ zeolite with half the lattice $NH_4^+$—on the basis of Uytterhoeven's stoichiometry—reveals the following differences between calculated and measured $H_2O$:

| Experiment A - activation for zero time at each temperature | |
|---|---|
| Temp., °F. | $H_2O$ Difference (g.mole) (Experimental-Calculated) |
| 572 | 0.107 |
| 752 | 0.071 |
| 932 | 0.046 |
| 1112 | 0.056 |

| Experiment B - activation at 750° F. | |
|---|---|
| Time, min. | $H_2O$ Difference (g.mole) (Experimental-Calculated) |
| 0 | 0.022 |
| 60 | −0.038 |
| 120 | 0.052 |
| 180 | 0.047 |
| 240 | 0.042 |

It is interesting to note that in most instances the excess $H_2O$ in the preceding table is about numerically equivalent to the residual sodium value of about 0.044 g. ion—all on the basis of 100 g. anhydrous base. Carter, Lucchesi and Yates, *J. PHYS. CHEM.*, 68, 1385-1391 (1964), described IR bands on NaX zeolite at 3400 and 1655 cm$^{-1}$ which persisted up to 450° C. (842° F.) and which they concluded were "due to residual hydrogen-bonded 'polymeric' water". It is probable that the $H_2O$ measured over and above that produced from intact and deaminated $NH_4^+$ sites is this hydrogen-bonded water structurally related to residual Na$^+$ species in the lattice.

In fact, the NaY zeolite itself may contain more than one kind of $H_2O$. For example, if it is assumed that the 0.414 g. ion Na$^+$ had one mole $H_2O$ associated—and that this represents strongly bound $H_2O$—then the $H_2O$ equivalent is 7.46 wt. % $H_2O$. This firmly bound $H_2O$ would represent 31% of the total 24.32 wt. % $H_2O$ found (Table 1). With $NH_4Y$, about 33% of the $H_2O$ was firmly bound enough to remain after one hour at 450° F.

Activation studies of two ammonium-, cerium-exchanged catalysts were made in a manner similar to those for $NH_4Y$.

Cerous nitrate exchange of $NH_4Y$ catalysts replaced most of the $NH_4^+$ ions with cerium but removed only 20-25% of the small residual sodium (Table 2). The $Ce^{3+}$-exchanged product, therefore, contained residues of $NH_4^+$ and Na$^+$. In contrast to $NH_4Y$ catalyst, the subsequently $Ce^{3+}$-exchanged material was able to lose $NH_4^+$ during activation down to a level of 0.01 mole/100 g. or less at 750° F. The $NH_4Y$ had required temperatures above 750° F. to accomplish this degree of removal.

The sum of chemical equivalents for $Na^+$, $NH_4^+$ and $Ce^{3+}$ after exchange was always noticeably less than the 0.414 g. ion $Na^+/100$ g. anhydrous base found with the original NaY zeolite. One explanation for this cation deficiency of the exchanged catalyst is that some protons are structurally incorporated during exchange but not directly measured by analysis. Chemically this incorporation is possible because the pH of the cerous nitrate solution was about 4.5, and favored cerous salt hydrolysis.

An increase in SiOH groups and a growing cation deficiency was observed as the catalyst became progressively deaminated during activation. However, the SiOH groups and intact $NH_4^+$ ions were not enough to account for all of the $H_2O$ measured by ignition loss at 1800° F. Total $H_2O$ measured was 0.16 to 0.10 mole/100 g. anhydrous base, but SiOH and $NH_4^+$ could not have produced more than 0.05 mole $H_2O$ on ignition.

The $NH_4Y$ study showed that residual sodium ions were complexed at a $H_2O/Na^+$ ratio of about 1. Continuation of this behavior in the $Ce^{3+}$-exchanged catalyst could at most produce 0.04 mole $H_2O$ on ignition. Therefore, the water not derivable from SiOH, $NH_4^+$ and $Na^+$ amounted to nearly half the measured $H_2O$. Another source was obviously contributing to the total.

Calculation of $(H_2O)/Ce^{3+}$ ratios, are shown for two 750° F. activations in Table 3. Calculation of $H_2O$ measured at 1800° F. does not imply the existence of associated molecular water but is equally capable of interpretation as $ce(OH)^{2+}$ species according to the equation:

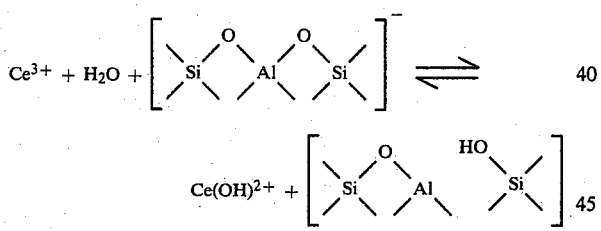

This correspondence of measured water to the amount needed for $Ce(OH)^{2+}$ formation indicates that substantially all of the cerium in Type Y zeolite activated at 750° F. (400° C.) is in this form or in an equivalent combination of such forms as $Ce^{+3}$, $Ce(OH)^{2+}$, $Ce(OH)_2^+$, $Ce^{+4}$ and $Ce(OH)^{+3}$.

A 750° F. activation with a sample of the same hydrated $CeNH_4Y$ zeolite in another experiment revealed an $H_2O/Ce^{3+}$ ratio of 1.041 (Table 4). Continuing this experiment at a series of temperatures up to 1292° F. (700° C.) showed a steady decline of the ratio to 0.370 with increasing temperature. Heating for up to 4 hr. at 750° F. did not lower the $H_2O/Ce^{3+}$ (or $Ce(OH)^{2+}/$total $Ce^{3+}$) ratio effectively below 1. $NH_4^+$ removal occurred during that time, and, thus, SiOH increased accordingly—as evidenced by the growing cation deficiency. $Ce(OH)^{2+}$, however, was far more stable, and that behavior in itself is more indicative of $Ce(OH)^{2+}$ than of $Ce(H_2O)^{3+}$. Only by increasing temperature above 750° F. could the fraction of total $Ce^{3+}$ in the $Ce(OH)^{2+}$ state be reduced.

Isoparaffin-olefin alkylations with $NH_4^+$—, $Ce^{3+}$—exchanged Type Y gave maximum alkylate yields and selectivity when the catalyst had been activated at about 750° F. rather than at lower or higher temperatures. Possibly, maximal $Ce(OH)^{2+}$ establishes the sites needed for isoparaffin-olefin alkylation. Also, $Ce^{3+}$-exchanged Type Y catalysts have been far more stable toward temperatures above 400° C. then $NH_4Y$, as measured by X-ray diffraction. When $Ce(OH)^{2+}$ sites become dehydroxylated, $Ce^{3+}$ and

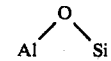

species can re-form. On the other hand, dehydroxylation of

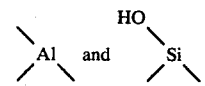

sites in deaminated $NH_4Y$ leads to a mixture of

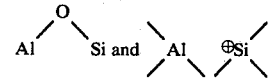

species, which could be less stable.

When we state that $Ce(OH)^{2+}$ sites are preferred for alkylation, we do not mean that these sites per se are the sole locus of activity. Rather, these sites form an essential part of a network or complex of sites, including

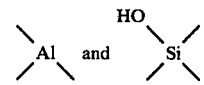

species. Very possibly the entire complex is required to achieve the carbonium ion-olefin combinations accompanied by good hydride transfer which are vital for a highly paraffinic alkylate. Structural considerations further suggest that only a portion of these complexes may be effective for alkylation, even though enough $H_2O$ for total $Ce(OH)^{2+}$ formation is a necessary ingredient of catalyst composition.

As is shown hereinafter, catalytic activity for paraffin-olefin alkylation is related to cerium content. ESR total spin counts of these catalysts with aromatics (such as benzene, perylene, anthracene, etc.) sorbed on them revealed a dependence of electron withdrawal ability upon cerium content. Calculations reveal about 5% of the cerium ions to be on the external catalyst surface and the data indicated a 1:1 numerical correspondence between these ceriums and the total spin count.

As is illustrated hereinafter in Example XIV, there is a nearly linear relation between the total ESR spin count of adsorbed aromatics on our cerium catalyst (when activated at temperatures below about 450° C.) and the alkylate yield under a given set of reaction conditions. In general the more preferred cerium-containing catalysts have total ESR spin counts above $3 \times 10^{19}/g$. with anthracene. Thus, there is a correlation between alkylate yield—with its essential dependence upon hydride transfer—and the electron withdrawal from anthracene by our catalyst.

EXAMPLE VIII

This example illustrates the use of substantially anhydrous acidic crystalline alumino-silicate zeolite as a paraffin-olefin alkylation catalyst. The activated 16-cycle $Ce^{+3}$/16-cycle $NH_4^+$-exchanged zeolite of Example VII was charged in amount of 23.3 g. into a one-liter, stirred autoclave containing a four-member baffle to diminish vortex formation. Then 444 milliliters of liquid isobutane was added. The stirring rate (of a six-member, flat-blade turbine) was adjusted such that substantially all of the zeolite was suspended in the liquid isobutane (about 550 rpm). The temperature in the reactor was raised to 80° C. using sufficient nitrogen to produce a total pressure of 250 p.s.i.g. Under these conditions nearly all of the hydrocarbon is in the liquid phase. Then a liquid mixture of one part by volume of butene-2 and five volumes of isobutane was charged from a Jerguson gauge via a needle valve and dip tube into the isobutane-catalyst slurry (and near the bottom of the reactor) at the rate of one milliliter of mixture per minute for a period of 220 minutes. Nearly all of the hydrocarbon was maintained in liquid phase. At the end of this time the reaction was stopped by cooling the reactor to 17° C., then separating the reaction mixture from the catalyst by first removing the normally gaseous hydrocarbons at room temperature and atmospheric pressure, and then separating the liquid product from the catalyst by filtration. The used catalyst analyzed 0.9% coke (nonvolatile residue). Some propane and n-butane but no methane, ethane, ethylene or propylene were found in the normally gaseous hydrocarbons. The $C_5^+$ *paraffin yield of the reaction mixture, based on the weight of olefin charged, was* 71.4% and the $C_5^+$ unsaturate yield was 0.24% on the same basis. Hereinafter all yield data are reported as based on the weight of olefin charged.

EXAMPLE IX

When the reaction of Example VIII was repeated except that the temperature was 120° C. and the pressure 475 p.s.i.g., the $C_5^+$ paraffin yield was 129.4% and the unsaturated $C_5^+$ hydrocarbon yield was 4.3%.

Table 5 further characterizes the $C_5^+$ product obtained in the reaction of Examples VIII and IX.

EXAMPLE X

This example illustrates the unexpectedly large increase in degree of conversion of olefin reactant to saturated $C_5^+$ hydrocarbon product when a small amount of a halide adjuvant is present in the reaction mixture. The reaction of Example VIII was repeated at 60° C. except that the catalyst used was the 32/16 zeolite of Example IV which had been prepared by 32 $NH_4^+$-exchange cycles followed by 16 $Ce^{+3}$-exchange cycles. The catalyst was activated by the procedure of Example VII. Without halide addition at 60° C., the yield of $C_5^+$ paraffins was 90% and the yield of $C_5^+$ unsaturate was 11.5%. On a mole basis this amounted to 0.44 mole of $C_5^+$ paraffins per mole of $C_4$ olefin charged. In contrast, when $2.4 \times 10^{-3}$ mole of tertiary butyl chloride (hereinafter, sometimes, TBC) was added to the reactor for each mole of initial isobutane, the yield of $C_5^+$ paraffins was 120% and $C_5^+$ unsaturates 6%. The TMP/$DMH_x$ ratio was 6.6. The used catalyst had no measurable coke content.

EXAMPLE XI

With the same proportion of t-butyl chloride the reaction of Example X was repeated at 40° C. (125 p.s.i.g.) and at 25° C. (125 p.s.i.g.). At 25° C. only 12% of $C_5^+$ paraffins was produced, and 0.49% of $C_5^+$ unsaturates. At 40° C. 120% of $C_5^+$ paraffins was produced and 6.5% of $C_5^+$ unsaturates. The TMP/$DMH_x$ ratio was 4.10 at 25° C. and 7.86 at 40° C.

EXAMPLE XII

When Example X was repeated at 120° C. (484 p.s.i.g.) without halide addition, 75% of $C_5^+$ paraffins and 1.1% of $C_5^+$ unsaturates were produced. The TMP/$DMH_x$ ratio was 3.16.

Of commercial importance is the finding that, by practice of our invention, we cannot only obtain good yields of alkylate which has a high TMP/$DMH_x$ ratio and is high in trimethylpentanes but that in these trimethylpentanes there is a low proportion of the less desirable 2,2,4-trimethylpentane (regarding this undesirability, see U.S. Pat. No. 2,646,453).

EXAMPLE XIII

Table 5 reports the products obtained from similar runs at 80° C. using the activated catalyst of Example VIII with t-butyl chloride, n-propyl chloride or n-butyl chloride as adjuvants (at a level of $2.4 \times 10^{-3}$ mole of adjuvant per mole of initial isobutene).

It is interesting to note that 60° C. with the 16/16 catalyst produced no more than half as much alkylate as 80° C. with this catalyst. The 32/16 catalyst was not so responsive to temperature changes above 40° C. Again, as temperature decreased from 80° to 60° C., a shift toward a heavier product occurred ($C_9^+$), but the 2,2,4-TMP content was desirably low. When this isomer decreased, the largest gain was in 2,3,3-TMP, as it had been with the 32/16 catalyst.

Temperature is a useful device in elucidating catalyst differences. When a catalyst exchanged only with $NH_4^+$ (32/0) was tested at 120° C. without TBC promoter, it was less active than a 16/16 catalyst (Table 8). The $C_5^+$ paraffin yields were 109.5%, based on olefin charge, with 32/0 and 129.4% with 16/16.

Evaluating an $NH_4^+$-exchanged catalyst (16/0) with TBC relative to 16/16 at 80° C. revealed a more dramatic difference in alkylate yield and product distribution.

The 16/0 catalyst produced too little $C_8$ paraffin and too much $C_9^+$ and $C_5$. These factors could also be used to understand the importance of a polyvalent metal, such as cerium, on the catalyst. But testing catalysts at milder conditions is even more effective in uncovering differences between them, as shown by the data from 32/0, 16/16, and 16/0. Therefore, low operating temperatures can be used as a research tool in distinguishing among alkylation catalysts that appear to be more similar at relatively high temperatures.

EXAMPLE XIII

Table 5 reports the products obtained from similar runs at 80° C. using the activated catalyst of Example VIII with t-butyl chloride, n-propyl chloride or n-butyl chloride as adjuvants (at a level of $2.4 \times 10^{-3}$ mole of adjuvant per mole of initial isobutane).

Table 9 reports the products obtained from similar runs (but with more intimate premixing of the feed olefin and feed paraffin) using $CCl_4$, TBC and various other adjuvants and using either continuous or "pulsed" addition of the adjuvant to the reaction mixture. In this table, the amount of adjuvant is reported as millimoles per mole of feed olefin charged (m.mole/m. OC).

In run 606 of Table 9, the catalyst was preconditioned by contact with a solution of perylene in $CCl_4$. The perylene was quantitatively adsorbed by the catalyst along with some $CCl_4$. The catalyst developed a dark, intense, blue color upon contact with the perylene solution. Removal of residual $CCl_4$ by vacuum-pumping at ambient temperature caused the catalyst color to turn to black. This black catalyst was the catalyst used in run 606.

In run 600, the catalyst was preconditioned with carbon tetrachloride as a control experiment for 606. The catalyst developed an intense red color on contact with the $CCl_4$. Upon vacuum pumping, the red color disappeared. It is this "pumped" catalyst which was used in run 600.

Potential catalyst adjuvants are those halides, both organic and inorganic (e.g., $AlBr_3$, $BF_3$, $HBCl_2$, $AsCl_3$), which are capable, under the reaction conditions, or sufficient polarization to promote carbonium ion reactions or to have carboniogenic properties. For precise control of the reaction product distribution (or alkylate quality) and to prolong catalyst life, we prefer to avoid adjuvants which contain atoms other than hydrogen, carbon, bromine, fluorine and chlorine (although as seen in run 632, oxygen, as in the form of alcoholic OH groups, can be present in reaction mixture. Water, $C_1$ to $C_{10}$ saturated alcohols (e.g., tertiary butyl alcohol, cyclohexanol) or mixtures thereof can be used, per se, as adjuvants or in combination with halides. To avoid accumulation of large organic molecules at the catalyst surface, we prefer to avoid those organic halides wherein the organic radical has a critical diameter greater than about $9A°$, such as the chlorinated naphthenic waxes. Note, however, in Table 9, that perylene presorbed on the catalyst from $CCl_4$ solution did not act as a "poison" but allowed about 10 relative percent more $C_5^+$ paraffin yield than a control experiment with carbon tetrachloride alone. This carbon tetrachloride control experiment itself produced a better than 10 relative percent increase in $C_5^+$ paraffin yield over a similar experiment with tertiary butyl chloride and without $CCl_4$. In contrast, $NH_3$ presorbed on the catalyst acted as a poison, even when TBC was added continuously to the reactor.

Our preferred halide adjuvants, when present in solution in the reaction mixture at a level of from $1 \times 10^{-5}$ to $1 \times 10^{-1}$ mole per mole of $C_4$-$C_6$ isoparaffin reactant, are HF, HCl, HBr and the saturated halohydrocarbons containing at least one atom per molecule of bromine, chlorine or fluorine. Mixtures of these substances can also be used as adjuvants. Of these adjuvants, we prefer carbon tetrachloride and the aliphatic saturated monochloride having no more than six carbon atoms. When the isoparaffin reactant is predominantly isobutane, we prefer to use, as halide adjuvants, the aliphatic saturated monochlorides having 3 or 4 carbon atoms.

The adjuvant can also be added to the catalyst after the final washing, in the exchange procedure but, more preferably, is added to catalyst after activation, as by passing gaseous HCl through the catalyst at the final stage of activation (or while cooling catalyst after activation). It can be important, especially in our continuous process, to control the amount of adjuvant present in the reactor vapor space.

Although the previous examples are illustrative of practice of our invention, the yields of many of these examples based on the weight of olefin charged, can be improved upon since it is probable that some of the olefin feed was not consumed in the reaction, but was lost because of slight leakages from the reactor system. For example, Table 20 reports two runs, at 80° C., 250 p.s.i.g. with a catalyst similar to that of Example VIII, which were identical except that Run A utilized the same reactor system as in the previous examples and Run B utilized the same system but greater care was used to prevent loss of feed olefin from the system. It can be seen that the yield in Run B was 12 relative % greater than Run A.

The calculated F-1 clear octane number of the alkylate of Run B (excluding materials boiling higher than 2,2,4-trimethylhexane) was 98.0. This high octane number, in combination with the reported yield, is one indication of the commercial promise of our invention. Note that a similar calculation shows the novel alkylate of Example XIX (see Table 20) to have a 99.9 octane number.

EXAMPLE XIII

This example illustrates, in Table 21, the effect of the gas used in catalyst activation on the $C_5^+$ paraffin yield, obtained from the resulting catalyst. Also shown below is a brief summary of the effect on $C_5^+$ yield of the final activation temperature.

Activation technique of a $CeNH_4$ zeolite to produce CeH zeolite can be divided into three distinct parts, during each of which the catalyst is maintained at a definite temperature for a fixed time. First is a preliminary drying, for example, at about 65° C. Second is a dehydration, for example, at about 230° C., which removes virtually all of the adsorbed water but probably does not affect hydroxyls or other water-forming entities more firmly incorporated into the structure. Third is the final activation stage, which is characterized by $NH_4^+$ decomposition and a relatively small removal of water. The activated catalyst, however, contains a definite and reproducible amount of water.

Early in the solid alkylation catalyst research program it had been observed that 400° C. appeared to be a preferred temperature for catalyst activation in air. That observation has been verified with current techniques and more highly exchanged catalysts. The following yields are illustrative:

| Catalyst Base | Temperature of Air Activation | Run No. | Wt. % $C_5^+$ Yield Based on Olefin Charged | |
|---|---|---|---|---|
| | | | Paraffins | Unsaturates |
| $32NH_4^+$, $16Ce^{3+}Y$ | 325° C. | 842* | 29.4 | 0.99 |
| " | 400° C. | 782* | 119.0 | 5.85** |
| " | 500° C. | 844* | 113.2 | 1.83 |
| $16NH_4^+$, $16Ce^{3+}Y$ | 400° C. | 868*** | 125.8 | 0.24 |
| " | 400° C. | 880*** | 133.8 | 0.36 |
| " | 500° C. | 860*** | 107.8 | 1.96 |

| Catalyst Compositions (wt. %, ignited basis) | | |
|---|---|---|
| Run No. | wt. % cerium | wt. % sodium |
| 782 | 14.0 | 0.31 |
| 842, 844 | 13.7 | 0.23 |

| 860, 868, 880 | 14.1 | 0.98 |

*Operating Conditions: 60° C., 200 psig., 220 min., i-C$_4$/C$_4$-ene = 14.9 min.
**Use of less preferred charge stock preparative technique for this run should not have affected C$_5$+ paraffin yield but probably increased the unsaturate yield.
***Operating Conditions: 80° C., 250 psig., 250 min., i-C$_4$/C$_4$-ene = 14.9 min.

With the 32NH$_4$+-, 16Ce$^{3+}$Y-catalyst, a 5.8% loss of C$_5$+ paraffin yield was obtained after activation at 500° C. relative to 400° C. With the 16NH$_4$+-, 16Ce$^{3+}$Y- catalyst, a 22.0% mean loss of C$_5$+ paraffin yield was obtained by activation at 500° C. instead of 400° C. The poor result following 325° C. activation may be a result of incompletely developed acidity in the solid or of residual ammonium, even though a negative test for ammonia evolution had been observed at the end of this activation. DTA and EGA experiments have shown that ammonium decomposition occurs at 300°-320° C. with NH$_4$Y zeolite.

To some extent the bound water lost on activation at higher than optimum temperature can be re-introduced to the catalyst. A hydrated CeNH$_4$Y zeolite was activated by the procedure of Example VII, the final heating stage being at 400° C. The resulting activated catalyst was contacted with an isobutane-butene-2 feed to produce a 141.5% yield of C$_5$+ paraffin.

A similar alkylation with a similar catalyst which had been activated at 600° C. in the final step produced only 128.5% of C$_5$+ paraffin.

A catalyst from a similar 600° C. activation was allowed to rehydrate (by exposure to humid air) until the rehydrated zeolite had reached equilibrium. This equilibrated zeolite was then reactivated at 400° C. When an isobutane-butene-2 feed was contacted with this rehydrated, reactivated catalyst, a 140.5% yield of C$_5$+ paraffin was obtained.

EXAMPLE XIV

This example illustrates the correlation between alkylate yield and Electron Spin Resonance (ESR) measurements of total spin count when aromatic hydrocarbons are adsorbed on the CeHY zeolite catalyst.

Several kinds of aromatic hydrocarbons (benzene, p-xylene, naphthene, anthracene, perylene, etc.) were adsorbed upon CeHY catalysts prepared by varied numbers of Ce+ and NH$_4$+ exchange cycles and with various types of activation (e.g., temperature, type of gas). The total ESR spin count of the adsorbed hydrocarbon was then measured. The sorption of the aromatics corresponded to the order of decreasing ionization potential (benzene being first). Catalysts with a higher degree of exchange produced larger spin counts with any particular aromatic. When C$_5$+ paraffin yields obtained with similar catalysts were plotted versus the spin count with a particular aromatic on each catalyst, a good correlation was achieved.

The most satisfactory correlations are for compounds having ionization potentials equal to or larger than that of naphthalene (about 8 ev.). Spin counts of compounds with lower ionization potential changed less than one order of magnitude while relatively large differences in alkylate yield were being observed. These correlations imply a relationship between radigenic nature of a catalyst and its performance in an alkylation reaction (which is highly dependent upon hydride transfer).

A far more exact relation between alkylate yield and anthracene spin count was realized when a series of catalysts of increasing cerium but constant sodium content was used. Anthracene spin count increased less after a (Ce$^{3+}$/NH$_4$+) equivalent ratio of about 2.5 had been reached.

Note, for example, a nearly linear relation between alkylate yield and anthracene spintcount can be seen by plotting the data below:

| Sorbed Hydrocarbon | Wt. % C$_5$+ paraffin based on wt. of olefin charged | Spin Count (Spins/g.Cat.) × 10$^{-19}$ |
|---|---|---|
| Anthracene | | |
| Cat. A | 91 | 1.2 |
| Cat. B | 126 | 2.4 |
| Cat. C | 150 | 3.8 |

Note:
Reactions at 80° C., Example VIII conditions with "improved feed premixing", isobutane-butene-2 feed. Sodium in catalyst 11 to 13% of cation capacity of zeolite.

Poor hydride transfer, as represented by C$_5$+ unsaturate formation, was intensified at low (Ce$^{3+}$/NH$_4$+) equivalent ratio. Other aspects of product quality—low C$_9$+, high C$_8$, and high TMP in the C$_8$—also improved when this composition ratio increased.

These data offer excellent support for the importance of the cerium in CeHY catalyst for alkylation and strongly imply a relation between hydride transfer facility of a catalyst and its electron withdrawal ability.

In our process the preferred mean residence time is in the range of 0.05-0.5 hour, more preferably 0.1 to 0.4 hour.

An illustration of the calculation of mean residence time, for the first 60 minutes in the reaction illustrated by FIGS. 1 and 2 in application Ser. No. 716,190, follows:

(444 ml. i-butane) (0.5543) = 246.11 g. isobutane for entire time
23.3 g. of catalyst
Change 1 vol. butene-2(density = 0.5988 g./ml.)
    5 vol. isobutane(density = 0.5543 g./ml.)
    (6) (D*) = (5) (0.5543) + (1) (0.5988)
             = 2.7715 + 0.5988 = 3.3703
    D* = density of hydrocarbon mixture = 0.5617
For 60 min.

$$246.11 + \frac{(1 \text{ hour})(23.3 \text{ grams catalyst})}{\frac{(60 \text{ min.})(1 \text{ ml./min.})(0.5617 \text{ g./ml.})}{2}} =$$

$$0.08861 \text{ hr.}/\frac{(\text{g. Hydrocarbon})}{(\text{g. Catalyst})}$$

EXAMPLE XV

This example illustrates the effect that catalyst composition has on the yield of C$_5$+ reaction product and on the product distribution, in particular with regard to the proportion of C$_8$ paraffins and the distribution of these C$_8$ paraffins into trimethylpentanes and dimethylhexanes.

The process of Example VIII was repeated except that the reaction temperature was 120° C. (which was close to the critical temperature of the reaction mixture), the reaction pressure was 500 p.s.i.g., and the reaction time was 3.67 hours. Separate runs were made with equal weights (activated basis) of zeolites of varied Na, H and polyvalent metal contents, which were prepared similarly to the catalysts of Examples II, III, IV and V.

Runs were also made, at 80° C., 250 p.s.i.g., and 2.4×10$^{-3}$ moles t-butyl chloride per mole of initial i-butane, with catalysts prepared from the following: the 1.72% (ignited) Ce zeolite of Example VII; a 16- cycle ammonium-exchanged NaY zeolite which was further exchanged with 16 cycles of a 13.3 g./l. aqueous solution of La(NO$_3$)$_3$.6H$_2$O; a 16-cycle ammonium-exchanged NaY zeolite which was further exchanged with 16 cycles of a 13.3 g./l. aqueous solution of hydrated mixed rare earth nitrates (approximate salt analysis, 48% Ce$_2$O$_3$, 24% La$_2$O$_3$, 17% Nd$_2$O$_3$, 5% Pr$_2$O$_3$, 3% Sm$_2$O$_3$, 2% Gd$_2$O$_3$); and, a 16-cycle ammonium exchanged NaY zeolite which was further exchanged with 16 cycles of aqueous Ce(NO$_3$)$_3$.6H$_2$O (as in Example IV).

All of these catalysts were activated by the procedure of Example VII.

The yields of the C$_5$+ paraffin and C$_5$+ unsaturates, based on the weight percent of olefin charged, the C$_5$+ paraffin distribution and the C$_8$ paraffin distribution of the products are shown in Table 11.

The yields and product distributions shown in Table 11 indicate that, in substantially anhydrous acidic crystalline alumino-silicate zeolites which have been prepared by ammonium exchange of sodium zeolites with ammonium ions and polyvalent metal ions, the catalytic activity and selectivity in paraffin-olefin alkylation are dependent upon the amount and type of exchanged polyvalent metal and the degree of "protonation" or "cationic deficiency" (which is related to the nitrogen content before activation). Therefore, when other reaction variables are fixed, an appropriate selection of the catalyst can be used to vary the yield and product distribution in our process.

Table 12 and Table 13 illustrate the effect on the ultimate catalyst of the type of salt used in the exchange solution.

It is evident from Table 13 that the yield differences are not determined only by the total amount of rare earth metal present. Therefore, it appears that different cations and their accompanying anions can have pronounced effects on catalyst performance. Other desirable catalysts can be prepared by exchanging NH$_4$Y zeolite with salts of Gd$^{+3}$, Dy$^{+3}$ and Sm$^{+3}$.

One precaution to be taken with data from Table 13 concerns the apparent gain in selectivity for C$_8$ paraffins with the La(NO$_3$)$_3$ and CeCl$_3$ catalysts. In fact, this gain is more in line with the selectivity gain which is typical when our process is operated at a relatively low degree of reactant conversion or product yield. In other words, if the Ce(NO$_3$)$_3$ catalyst had been used to produce only 68 to 73% C$_5$+ paraffin yield (the range for La(NO$_3$)$_3$ and CeCl$_3$), the molar C$_8$ paraffin content of the C$_5$+ paraffins would have increased to about 80% instead of remaining at the 69.0% actually observed at 132.0% C$_5$+ paraffin yield.

As shown by these data, the anion in the exchange solution exerts an influence on catalyst performance. The effect is related to the condition of metal cations in aqueous solution as a function of anion, cation concentration, pH and temperature. An effect such as the following is the probable cause:

Other cations which can affect the catalyst are the alkali metals, such as lithium, sodium, potassium and cesium. As shown in Table 14, at comparable sodium levels, C$_5$+ paraffin yield progressed from 26 to 132 wt.% olefin charge for an increase of cerium from 2.0 to 13.5%. Even at 8.3% cerium, the C$_5$+ paraffin yield was only 62.7% on the same basis. The probability that the 1.68% sodium content did not have the principal deleterious effect upon this 62.7% yield is supported by the 118.9% yield for a catalyst containing 2.8% sodium but 13.0% cerium and by the 115.4% yield for another catalyst with a 1.68% sodium and a 12.8% cerium content.

Some gain in C$_5$+ paraffin yield (115.4 to 132.0) can be inferred for a reduction in sodium content from 1.68 to 0.76%.

Selectivity effects of cerium are illustrated by the relatively high C$_5$+ unsaturate production with catalysts containing less than about 12% cerium. Trimethylpentane/dimethylhexane (TMP/DMH$_x$) ratios were also comparatively low for those catalysts, and relatively undesirable C$_9$+ paraffins constituted as much as 27.2 mole % of the total C$_5$+ paraffins for the lowest cerium catalyst. These data show that with less than about 12% cerium, alkylate will be not only lower in yield but also poorer in quality.

A series of NH$_4$+-, Ce$^{3+}$-exchanged catalysts having very similar sodium levels clarified the essential role of cerium in producing favorable yields of high quality alkylate.

When cerium replaced ammonium on a Type Y zeolite at constant sodium level, the following effects were observed:

1. Appreciable gains were realized in C$_5$+ paraffin yield, in relative proportion of C$_8$ paraffins, and in selectivity for trimethylpentanes (TMP/DMH$_x$ ratio).
2. Simultaneously, desirable decreases were found in C$_5$+ unsaturates and in the relative proportion of C$_9$+ paraffins.
3. The only undesirable trend was an increase in the relative amount of 2,2,4-TMP up to 26.4 mole % of the total TMP. However, typical sulfuric acid alkylates have 2,2,4-TMP contents above 40%. This isomer has the lowest F-1 octane number of all the TMP.
4. The largest gains in yield and selectivities occurred at values of (Ce$^{3+}$/NH$_4$+) equivalent ratio below about 2.5. Higher ratios are desirable, but corresponding product improvements become smaller.

These catalysts were prepared from the same common lot of NH$_4$+-exchanged Type Y zeolite. The following analytical data establish that Ce$^{3+}$ was exchanging for NH$_4$+ and that no net loss of Na+ occurred from the NH$_4$+-exchanged zeolite:

| Catalyst No. | Analysis (g. equivalent/100 g. anhydrous residue) | | | |
| --- | --- | --- | --- | --- |
| | Na | NH$_4$+ | Ce$^{3+}$* | Σ |
| FX10 | 0.064 | 0.389 | — | 0.543 |
| FX10-1-2 | 0.054 | 0.190 | 0.175 | 0.419 |
| FX10-1-3 | 0.047 | 0.102 | 0.253 | 0.402 |
| FX10-1-4 | 0.047 | 0.049 | 0.299 | 0.395 |

*Average of 3 analyses

The original zeolite had a sodium content of 0.426 equiv./100 g. anhydrous residue after correction for 1800° F. ignition loss. Residual sodium content was thus 11–13% of the original.

Another interesting but undecided aspect of these catalysts is their growing cation deficiency as cerium exchange increases. A deficiency is said to occur when the sum of residual sodium, ammonium and rare earth does not equal the positive charged initial sodium. The presence of protons—bound or "solvated"—can account for the apparent deficiency.

As has been shown in Examples I to VII, we prefer to prepare the substantially anhydrous acidic alumino-silicate zeolites which are prepared from crystalline sodium zeolites by first exchanging the bulk of the sodium with ammonium ions and then exchanging the resulting zeolite, which is low in sodium and high in ammonium ions, with solutions of polyvalent metal cations. When the base zeolite is sodium Y, the ammonium-exchanged zeolite should contain, on an ignited basis, less than 3% Na and preferably less than 1.0% Na.

In our ammonium exchange we also prefer that the sodium content of the exchange solution be kept as low as is practicable. One means of removing sodium ions from ammonium salt solutions is by a separate cation exchange of the solution with a bed of ammonium-containing ion-exchange resins or non-crystalline ammonium zeolites. In this sodium-ion removal step, which is particularly advantageous in continuous ammonium exchange (as in the procedures of Example II), the sodium ion in the ammonium-ion exchange solution exchanges with the ammonium ion in the resin and the resulting ammonium-rich solution is recycled to the vessel containing the crystalline zeolite for additional exchange with the sodium in the zeolite. The ion-exchange resin bed (or noncrystalline zeolite bed) can be regenerated by contacting the ammonium-sodium equilibrium resin with an ammonium-rich stripping stream. The sodium-rich effluent from the regeneration is discarded after, if desired, residual ammonia has been recovered by flash distillation.

Products obtained from a preferred Gd catalyst and from two other, less preferred, catalyst types are shown in Table 22. One of the two less preferred catalysts was obtained by activation (as in Example VII but with 8 hours at 400° C. to insure good $NH_3$ removal) of a highly (16 cycles) ammonium-exchanged type Y zeolite (to produce HY catalyst). The HY catalyst produced only about one-fourth as much alkylate, together with more $C_9+$ and $C_5$ and less $C_8$, as its cerium counterpart.

The other less preferred catalyst was prepared by activation of a 16-cycle cerium exchanged, 16-cycle ammonium-exchanged sodium X zeolite (to produce CeHX catalyst). In comparison with CeHY catalyst (run 664) the CeHX catalyst produced an appreciably smaller $C_5+$ paraffin yield. An Analysis of this paraffin product showed 23.9 mole % to be isopentane (which is 2 to 4 times the isopentane usually found in alkylate produced by CeHY catalyst). Accordingly, the $C_8$ paraffin in the alkylate produced by the CeHX was only 59 mole % compared with about 70% for CeHY.

Runs 628 and 674 were made with catalysts prepared by an exchange procedure similar to that of Example IV and activated as in Example VII (except that for the run 674 catalyst helium was substituted for air), but wherein gadolinium nitrate was used instead of cerium nitrate in the exchange solution. The resulting novel Gd-aluminosilicate, upon activation, produced a novel catalyst which is very useful for hydrocarbon conversion, for example, see Table 22. GdHY zeolite, which can be prepared by activation of a crystalline $GdNH_4Y$ (or $GdNaHNH_4Y$) zeolite (e.g. obtained by Gd-cation exchange of highly ammonium-exchanged sodium Y zeolite), is also useful as an alkylation catalyst.

In the Gd alumino-silicate catalyst, at least 25% and, preferably, at least 40% of the electronegativity associated with the alumino-silicate framework is satisfied by cations of gadolinium or of its oxides or hydroxides. When the Gd catalyst contains less than one alkali metal cation (e.g. $Na^+$) for every 4 aluminum atoms in the alumino-silicate framework, the catalyst is especially useful for such hydrocarbon conversion reactions as isomerizing polycyclic aromatic hydrocarbons, paraffin-olefin alkylation and the cracking of gas oil. Preferably, the alumino-silicate zeolite is crystalline and is chemically characterized by the empirical formula $M_x(AlO_2)_x(SiO_2)_y \cdot (H_2O)_z$, where x, y and z are integers, the ratio x/y being from 1.0 to 0.2 and where M is chosen from at least one of the following groups:

(1) at least one $Gd^{+3}$ cation for every 12 atoms of aluminum in the alumino-silicate framework of said zeolite;

(2) at least one cation of $Gd(OH)^{+2}$ for every 8 atoms of aluminum in the alumino-silicate framework of said zeolite;

(3) at least one cation of $Gd(OH)_2^{+1}$ for every 4 atoms of aluminum in the alumino-silicate framework of said zeolite;

(4) a combination of the members of at least two of the above groups;

and wherein the balance of the cations necessary for electronic equivalency comprises $H^+$ or cations of metals, metal oxides or metal hydroxides and wherein there is less than one alkali metal cation for every four atoms of aluminum in the alumino-silicate zeolite, more preferably, less than one alkali metal cation for every ten atoms of aluminum.

The Gd zeolite can contain as such additional cations, the cations of magnesium, aluminum, silver, nickel, zinc, cerium, lanthanum and mixtures of these cations. In such catalysts it is preferred that at least one such cation is present for every 20 atoms of aluminum in the alumino-silicate framework of said zeolite.

For most hydrocarbon conversions, the ratio x/z in the empirical formula of the zeolite should be in the range of 0.25 to 2. If excess water is present, the zeolite should be "activated" by heating according to the procedure disclosed in the aforementioned applications of Kirsch, Barmby and Potts. If the zeolite is deficient in "bound" water, water can be added, as by exposure to steam in air or nitrogen.

As used herein, the term "framework", in reference to the alumino-silicate portion of the zeolite (which can be crystalline or amorphous), excludes those aluminum ions which are in exchange positions and which are neutralizing some of the negative charge associated with the aluminum atoms in the alumino-silicate tetrahedra of the zeolite. Note that aluminum in the alumino-silicate framework can be either trigonal or tetrahedral.

For such reactions as reforming, aromatization, hydrogen transfer, hydrocracking and hydroisomerization, it is preferred that the catalyst have incorporated therewith from 0.05 to 25% (more preferably, 0.05 to 5%) of a hydrogenation catalyst component containing a hydrogen-active metal such as platinum, palladium, rhodium, rhenium, ruthenium, molybdenum, cobalt or nickel (or a chemical compound, as an oxide or sulfide, of such a metal).

TABLE 1

Exchanged Zeolite Catalysts
Chemical Composition of Activated Equilibrated Ammonium-Only Catalyst Catalyst: 16 Exchange Cycles with NH₄NO₃ solutes, Dry Air Medium, Rotary Kiln

| Catalyst No. | | Activation Conditions Maximum Temperature °F. | Time**** | Weight Percent TIL* | | | Na-Equivalent Moles** | | |
|---|---|---|---|---|---|---|---|---|---|
| | | | | $Na^+$ | N | $H_2O$ | $Na^+$ | $NH_4^+$ | Σ |
| ***Base NaY Zeolite | | — | — | 9.51 | — | 24.32 | 0.414 | — | 0.414 |
| Base after $NH_4^+$ Exchange | | — | — | 1.04 | 5.50 | 23.76 | 0.045 | 0.393 | 0.438 |
| | Run No. | | | | | | | | |
| Experiment A | A-1 | 150 | 30 | 1.01 | 5.51 | 24.63 | 0.044 | 0.394 | 0.438 |
| | A-2 | 450 | 0 | 1.03 | 5.28 | 24.88 | 0.045 | 0.377 | 0.422 |
| | A-3 | 450 | 60 | 1.07 | 4.72 | 25.39 | 0.047 | 0.337 | 0.384 |
| | A-4 | 750 | 0 | 1.00 | 2.88 | 26.14 | 0.043 | 0.206 | 0.249 |
| | A-5 | 750 | 60 | 1.07 | 1.98 | 26.27 | 0.047 | 0.141 | 0.188 |
| | A-6 | 750 | 120 | 1.13 | 0.84 | 27.26 | 0.049 | 0.060 | 0.109 |
| | A-7 | 750 | 180 | 1.05 | 0.57 | 27.58 | 0.046 | 0.041 | 0.087 |
| | A-8 | 750 | 240 | 1.09 | 0.54 | 27.62 | 0.047 | 0.039 | 0.086 |
| Experiment B | B-1 | 150 | 30 | 1.03 | 5.42 | 24.54 | 0.045 | 0.387 | 0.432 |
| | B-2 | 450 | 0 | 1.03 | 5.04 | 25.07 | 0.045 | 0.360 | 0.405 |
| | B-3 | 450 | 60 | 1.16 | 4.74 | 25.17 | 0.050 | 0.339 | 0.389 |
| | B-4 | 572 | 0 | 1.14 | 4.41 | 25.44 | 0.050 | 0.315 | 0.365 |
| | B-5 | 752 | 0 | 1.15 | 3.33 | 26.17 | 0.050 | 0.238 | 0.288 |
| | B-6 | 932 | 0 | 1.17 | 0.48 | 27.43 | 0.051 | 0.034 | 0.085 |
| | B-7 | 1112 | 0 | 1.17 | 0.14 | 27.65 | 0.051 | <0.010 | <0.061 |
| | B-8 | 1292 | 0 | 1.14 | 0.13 | 25.19 | 0.050 | <0.009 | <0.059 |
| | B-9 | 1292 | 120 | 1.28 | 0.13 | 25.57 | 0.056 | <0.009 | <0.065 |

*TIL - True ignition loss corrected for ammonium.
**Na - Equivalent moles, moles/100 g. ignited catalyst (TIL).
***Molar ratio Na₂O/Al₂O₃ was 0.98. Molar ratio SiO₂/Al₂O₃ was 4.70.
****Time, in minutes, at indicated maximum temperature.

TABLE 2

Exchanged Zeolite Catalysts
Chemical Composition of Activated Ammonium Cerium Catalysts Activation Conditions: Rotary Kiln, Dry Air, Ambient pressure, Programed Temperatures, Air rate = 0.6SCFM

| Run No. | | Activation Conditions | | LOI* | Moles** | | | | |
|---|---|---|---|---|---|---|---|---|---|
| | | Max. Temp. °F. | Time*** | $H_2O$ | $Na^+$ | $Ce^{3+}$ | $NH_4^+$ | | $H_2O$ |
| Experiment C | | | | | | | | | |
| | C-1 | 150 | 30 | 17.21 | 0.037 | 0.097 | 0.025 | 0.354 | 0.937 |
| | C-2 | 450 | 0 | 10.25 | 0.037 | 0.096 | 0.054 | 0.379 | 0.523 |
| | C-3 | 450 | 60 | 5.21 | 0.038 | 0.096 | 0.068 | 0.394 | 0.228 |
| | C-4 | 750 | 0 | 4.05 | 0.038 | 0.097 | 0.043 | 0.371 | 0.186 |
| | C-5 | 750 | 60 | 3.38 | 0.034 | 0.098 | 0.020 | 0.350 | 0.169 |
| | C-6 | 750 | 120 | 3.56 | 0.036 | 0.098 | 0.014 | 0.345 | 0.186 |
| | C-7 | 750 | 180 | 3.09 | 0.033 | 0.098 | <0.009 | <0.336 | 0.163 |
| | C-8 | 750 | 240 | 3.40 | 0.035 | 0.098 | <0.009 | <0.337 | 0.180 |
| Experiment D | | | | | | | | | |
| | D-1 | 150 | 30 | 19.58 | 0.038 | 0.096 | 0.056 | 0.381 | 1.044 |
| | D-2 | 450 | 0 | 13.18 | 0.042 | 0.092 | 0.056 | 0.373 | 0.721 |
| | D-3 | 450 | 60 | 6.89 | 0.038 | 0.094 | 0.056 | 0.375 | 0.333 |
| | D-4 | 750 | 0 | 4.89 | 0.039 | 0.098 | 0.054 | 0.388 | 0.222 |
| | D-5 | 750 | 60 | 3.92 | 0.038 | 0.099 | 0.031 | 0.365 | 0.189 |
| | D-6 | 750 | 120 | 3.80 | 0.038 | 0.099 | 0.041 | 0.375 | 0.174 |
| | D-7 | 750 | 180 | 3.76 | 0.037 | 0.100 | 0.014 | 0.352 | 0.197 |
| | D-8 | 750 | 240 | 3.47 | 0.040 | 0.101 | 0.010 | 0.352 | 0.183 |
| Experiment E | | | | | | | | | |
| | E-1 | 150 | 30 | 15.09 | 0.037 | 0.096 | 0.051 | 0.376 | 0.796 |
| | E-2 | 450 | 0 | 9.76 | 0.043 | 0.098 | 0.051 | 0.387 | 0.497 |
| | E-3 | 450 | 60 | 5.08 | 0.042 | 0.090 | 0.057 | 0.370 | 0.230 |
| | E-4 | 572 | — | 4.84 | 0.043 | 0.099 | 0.057 | 0.396 | 0.216 |
| | E-5 | 752 | — | 4.08 | 0.041 | 0.098 | 0.049 | 0.384 | 0.182 |
| | E-6 | 932 | — | 3.04 | 0.040 | 0.097 | 0.012 | 0.341 | 0.157 |
| | E-7 | 1112 | — | 2.70 | 0.043 | 0.098 | <0.009 | <0.347 | 0.127 |
| | E-8 | 1292 | 0 | 2.24 | 0.045 | 0.100 | <0.009 | <0.355 | 0.116 |
| | E-9 | 1292 | 120 | 1.66 | 0.034 | 0.099 | <0.009 | <0.340 | 0.083 |

*LOI - Loss on ignition (includes ammonium)
**Moles/100 g ignited catalyst (TIL)
***Time, in minutes at indicated maximum temperature.

TABLE 3

Exchanged Zeolite Catalysts
Water-cerium Ratio for Ammonium-Cerium Exchanged
Zeolite Catalysts Activated at Constant Temperature for Different Times
Basis of Data: Moles ion/100 g anhydrous base[3]
$16NH_4^+$ exchanges followed by $16Ce^{3+}$ exchanges
Activation Conditions: Rotary Kiln, Dry Air, Ambient Pressure,
Programmed Temperatures, Air Rate = 0.06 SCFM

| Run No. | Temp. (°F.) | Time at Temp. (min) | $\Delta^{(1)}$ | Non-Ce $H_2O^{(2)}$ SiOH | Non-Ce $H_2O^{(2)}$ $Na^+$ | Non-Ce $H_2O^{(2)}$ $NH_4^+$ | Total Non-Ce $H_2O$ | Total $H_2O$ | $H_2O$ For Ce | Ce (moles) | $\dfrac{Ce(OH)^{2+}}{Ce} \left(= \dfrac{H_2O}{Ce^{3+}}\right)$ |
|---|---|---|---|---|---|---|---|---|---|---|---|
| Experiment C | | | | | | | | | | | |
| C-1 | 450 | 60 | 0.020 | 0.010 | 0.037 | 0.034 | 0.081 | 0.228 | 0.147 | 0.096 | 1.531 |
| C-4 | 750 | 0 | 0.043 | 0.022 | 0.038 | 0.021 | 0.091 | 0.186 | 0.095 | 0.097 | 0.980 |
| C-5 | 750 | 60 | 0.064 | 0.032 | 0.034 | 0.010 | 0.076 | 0.169 | 0.093 | 0.098 | 0.949 |
| C-6 | 750 | 120 | 0.069 | 0.034 | 0.036 | 0.007 | 0.077 | 0.186 | 0.109 | 0.098 | 1.113 |
| C-7 | 750 | 180 | 0.092 | 0.046 | 0.033 | 0.002 | 0.071 | 0.163 | 0.092 | 0.098 | 0.938 |
| C-8 | 750 | 240 | 0.085 | 0.042 | 0.035 | 0.000 | 0.077 | 0.180 | 0.103 | 0.098 | 1.051 |
| | | | | | | | | | Mean of last five values = | | 1.006 |
| Experiment D | | | | | | | | | | | |
| D-3 | 450 | 60 | 0.035 | 0.018 | 0.038 | 0.028 | 0.084 | 0.0333 | 0.249 | 2.649 | |
| D-4 | 750 | 0 | 0.022 | 0.011 | 0.039 | 0.027 | 0.077 | 0.222 | 0.145 | 0.098 | 1.480 |
| D-5 | 750 | 60 | 0.045 | 0.022 | 0.038 | 0.016 | 0.076 | 0.189 | 0.113 | 0.099 | 1.142 |
| D-6 | 750 | 120 | 0.035 | 0.018 | 0.037 | 0.076 | 0.076 | 0.174 | 0.098 | 0.099 | 0.990 |
| D-7 | 750 | 180 | 0.058 | 0.029 | 0.037 | 0.007 | 0.073 | 0.197 | 0.124 | 0.100 | 1.240 |
| D-8 | 750 | 240 | 0.058 | 0.029 | 0.040 | 0.005 | 0.074 | 0.183 | 0.109 | 0.101 | 1.079 |
| | | | | | | | | | Mean of last five values = | | 1.186 |
| | | | | | | | | | Mean of last four values = | | 1.112 |

[1] $\Delta$ = [(Molar equivalent $Na^+$ in Na Base) − (Molar equivalents of measured ions in catalyst)]/100 g anhydrous base
[2] Non-$Ce_2O$ calculated as $2SiOH \rightarrow 1H_2O$ & $2NH_4^+ \rightarrow 1H_2O$.
[3] Anhydrous base = ignited catalyst to which is added as $NH_4^+$, $NH_3$ evolved on ignition at 1800° F.

TABLE 4

Exchanged Zeolite Catalysts
Water-cerium Ratio for Ammonium-Cerium Exchanges
Zeolite Catalysts Activated at Different Temperatures
Basis of Data: Moles ion/100 g anhydrous catalyst
Catalyst: $16NH_4^+$ exchanges followed by $16Ce^{3+}$ exchanges
Activation Conditions: Rotary kiln, Dry air, Ambient pressure,
Programed temperatures, Air Rate = 0.6 SCFM

| Run No. | Temp (°F.) | Time at Temp. (min) | $\Delta^{(1)}$ | Non-Ce $H_2O^{(2)}$ SiOH | Non-Ce $H_2O^{(2)}$ $Na^+$ | Non-Ce $H_2O^{(2)}$ $NH_4^+$ | Total Non-Ce $H_2O$ | Total $H_2O$ | $H_2O$ for Ce | Ce (moles) | $H_2O$/Ce Ratio | % Max. OH |
|---|---|---|---|---|---|---|---|---|---|---|---|---|
| E-3 | 450 | 60 | 0.044 | 0.022 | 0.042 | 0.028 | 0.092 | 0.230 | 0.138 | 0.090 | 1.533 | 106 |
| E-4 | 572 | 0 | 0.018 | 0.009 | 0.043 | 0.028 | 0.080 | 0.216 | 0.136 | 0.099 | 1.375 | 100 |
| E-5 | 752 | 0 | 0.030 | 0.015 | 0.041 | 0.024 | 0.080 | 0.182 | 0.102 | 0.098 | 1.041 | 84 |
| E-6 | 932 | 0 | 0.073 | 0.036 | 0.040 | 0.006 | 0.082 | 0.157 | 0.075 | 0.097 | 0.733 | 77 |
| E-7 | 1112 | 0 | 0.072 | 0.036 | 0.043 | 0.002 | 0.081 | 0.127 | 0.046 | 0.098 | 0.470 | 59 |
| E-8 | 1292 | 0 | 0.069 | 0.034 | 0.045 | 0.000 | 0.079 | 0.116 | 0.037 | 0.100 | 0.370 | 54 |
| E-9 | 1292 | 120 | 0.083 | 0.042 | 0.034 | 0.000 | 0.076 | 0.083 | 0.007 | 0.009 | 0.077 | 39 |

[1] $\Delta$ = [(Molar equivalent $Na^+$ in Na-Base) − (Molar equivalents of measured ions in catalyst)]/100 g anhydrous base
[2] Non-Ce $H_2O$ calculated as $2SiOH \rightarrow 1H_2O$ & $2NH_4^+ \rightarrow 1H_2O$.
[3] Anhydrous base = ignited catalyst to which is added, as $NH_4^+$, the $NH_3$ evolved on ignition at 1800° F.

TABLE 5

ISOBUTANE-BUTENE-2 ALKYLATION WITH ZEOLITE CATALYST

| Example No. | VIII | IX | XIII | XIII | XIII* |
|---|---|---|---|---|---|
| | | | t-Butyl Chloride | n-Propyl Chloride | n-Butyl Chloride |
| Adjuvant | None | None | | | |
| Reaction Temp. | 80° C. | 120° C. | 80° C. | 80° C. | 80° C. |
| Reaction Press. (psig.) | 250 | 475 | 250 | 250 | 250 |
| Wt. % $C_5^+$ Paraffin Yield, based on olefin charged | 71.4 | 129.4 | 142.8 | 129.6 | 117.2* |
| $C_5^+$ Paraffin Dist., Mole % | | | | | |
| $C_9^+$ | 4.5 | 10.7 | 14.1 | 5.8 | 10.1 |
| $C_8$ | 67.3 | 54.7 | 60.1 | 63.3 | 71.5 |
| $C_7$ | 5.1 | 12.0 | 5.9 | 5.7 | 7.1 |
| $C_6$ | 4.2 | 8.9 | 4.6 | 4.2 | 5.9 |
| $C_5$ | 19.0 | 13.7 | 15.3 | 21.0 | 5.4* |
| Wt. % $C_5^+$ Unsaturate Yield based on olefin charged | 0.24 | 4.34 | 3.54 | 0.24 | 0.49 |
| $C_8$ Paraffin Dist., Mole % | | | | | |
| Trimethylpentanes | 88.2 | 74.0 | 82.4 | 88.1 | 85.0 |
| Dimethylhexanes | 11.8 | 24.6 | 16.6 | 11.9 | 14.9 |
| Methylheptanes | 0.0 | 1.5 | 1.1 | 0.0 | 0.1 |
| TMP/$DMH_x$ Ratio** | 7.47 | 3.01 | 4.98 | 7.38 | 5.71 |

TABLE 5-continued

ISOBUTANE-BUTENE-2 ALKYLATION WITH ZEOLITE CATALYST

| Example No. | VIII | IX | XIII | XIII | XIII* |
|---|---|---|---|---|---|
| Adjuvant | None | None | t-Butyl Chloride | n-Propyl Chloride | n-Butyl Chloride |
| % 2,2,4 in TMP*** | 26.9 | — | 21.0 | 25.0 | 23.0 |

In Ex. XIII halide concentration = 1.6 millimole/mole total hydrocarbon charged. 80° C., 250 psig, i-$C_4$-ane/$C_4$-ene = 14.9 molar (min.), 3.67 hr. $16NH_4^+$-, $16Ce^{3+}$-Catalyst (10.13% Ce, 0.68% Na-before 400° C. max. activation) with an ignition loss = 24.37% at 1800° F. Feed introduced into bottom of Jerguson gauge.
*One product gas sample was lost. Some isopentane thereby not accounted for, and the $C_5^+$ yield and distribution are affected.
**Mole ratio trimethylpentanes to dimethylhexanes.
***Mole percent 2,2,4-trimethylpentane in total trimethylpentanes.

TABLE 9

ISOPARAFFIN-OLEFIN ALKYLATION WITH ZEOLITE CATALYSTS $CCl_4$ as Adjuvant
80° C., i-$C_4$-ane/$C_4$-ene-2 = 15 (min.), 3.67 hr., $NH_4^+$-, $Ce^{3+}$- Type Y

| Adjuvant | | | | | | | |
|---|---|---|---|---|---|---|---|
| Type | TBC | TBC | TBC* | TBC** | $CCl_4$ & TBC | TBC & TBA*** | $CCl_4$ |
| Technique | Continuous | Pulse | Pulse | Pulse | Continuous | Continuous | Continuous |
| Amount, mmole/m OC | 4.26 | 28.4 | 30.1 | 30.1 | 30.1 $CCl_4$ 20.2 TBC | 30.1 TBC 30.1 TBA | 30.1 |
| Run Number | 570 | 614 | 606 | 600 | 630 | 632 | 680 |
| $C_5^+$ Paraffin Yield, Wt. % OC | 162.1 | 150.0 | 193.4 | 176.3 | 141.1 | 150.1 | 178.5 |
| $C_5^+$ Unsaturates, wt. % OC | 0.00 | | 0.00 | | | | 0.04 |
| $C_5^+$ Paraffin Distribn., mole % | | | | | | | |
| $C_9^+$ | 9.1 | 4.6 | 7.3 | 5.8 | 4.1 | 5.0 | 5.8 |
| $C_8$ | 73.2 | 76.3 | 71.1 | 72.3 | 71.5 | 72.2 | 74.9 |
| $C_7$ | 7.3 | 7.3 | 7.1 | 7.1 | 6.8 | 7.0 | 7.5 |
| $C_6$ | 6.4 | 5.9 | 5.8 | 5.7 | 5.2 | 5.7 | 5.4 |
| $C_5$ | 4.0 | 5.9 | | | 12.4 | 10.2 | 6.4 |
| $C_8$ Paraffin Distribution | | | | | | | |
| TMP | 86.0 | 88.4 | 87.1 | 87.8 | 88.0 | 88.2 | 87.9 |
| $DMH_x$ | 13.7 | 11.6 | 12.9 | 12.0 | 11.9 | 11.8 | 12.1 |
| $MH_p$ | 0.3 | 0.0 | 0.0 | 0.2 | 0.0 | 0.0 | 0.1 |
| TMP Distribution | | | | | | | |
| 2,2,4- | 19.5 | 24.5 | 22.9 | 27.2 | 29.2 | 28.3 | 26.4 |
| 2,2,3- | 5.3 | 5.4 | 5.6 | 5.9 | 6.5 | 5.0 | 5.1 |
| 2,3,4- | 34.2 | 30.9 | 31.8 | 29.1 | 27.1 | 28.7 | 30.9 |
| 2,3,3- | 41.0 | 39.2 | 39.7 | 37.8 | 37.2 | 38.0 | 37.6 |

*Porylene (from $CCl_4$) presorbed on catalyst, TBC added continuously
**$CCl_4$ presorbed on catalyst, TBC added continuously
***TBA = t-butyl alcohol, TBC = t-butyl chloride

TABLE 10

| Paraffin | Isobutane*** | Isobutane*** | Isobutane*** | Isobutane*** | n-Butane**** | Isobutane*** | Isobutane**** |
|---|---|---|---|---|---|---|---|
| Olefin | 2-Methyl-butene-2 | 2-Methyl-butene-2 | Butene-2 | Butene-1 | Butene-1 | Butene-2 | Butene-2 |
| Temperature °C. | 120 | 120 | 120 | 120 | 80 | 80 | 80 |
| Pressure, psig. | 460 | 485 | 455 | 455 | 250 | 250 | 250 |
| Catalyst | | | | | | | |
| Wt. % Na (ignited) | 1.68 | 1.11 | 1.11 | 1.38 | 0.76 | 0.76 | 0.76 |
| Wt. % Ce (ignited) | 6.8 | 8.7** | 8.7** | 12.4 | 13.5 | 13.5 | 13.5 |
| $C_5^+$ Paraffin Yield Wt. % Olefin Chg. | 28.6 | 49.0 | 51.8 | 119.7 | 25.6 | 135.0 | 132.0 |
| $C_5^+$ Unsaturate Yield, Wt. % Olefin Chg. | 31.2 | 15.4 | 0.5 | 2.8 | 1.6 | 1.88 | 0.26 |
| $C_5^+$ Paraffin Dist., Mole % | | | | | | | |
| $C_9^+$ | 32.5 | 29.2 | 4.2 | 9.7 | 26.6 | 14.6 | 8.0 |
| $C_8$ | 32.6 | 36.6 | 82.8 | 55.0 | 25.6 | 69.3 | 69.0 |
| $C_7$ | 15.6 | 10.3 | 6.2 | 12.0 | 2.0 | 6.7 | 6.1 |
| $C_6$ | 15.2 | 10.3 | 5.2 | 11.4 | 2.0 | 5.5 | 5.2 |
| $C_5$ | 4.0 | 13.6 | 1.6 | 11.9 | 43.8 | 4.0 | 11.7 |
| $C_8$ Paraffin Dist., Mole % | | | | | | | |
| Trimethyl-pentanes | 71.2 | 74.7 | 63.8 | 75.7 | 33.7 | 85.4 | 88.0 |
| Dimethyl-hexanes | 26.4 | 24.3 | 36.4 | 23.1 | 65.6 | 14.6 | 12.0 |
| Methylheptanes | 2.4 | 1.0 | 0.7 | 1.2 | 0.7 | 0.0 | 0.0 |

*= 2.4 × $10^{-3}$ mole tertiary butyl chloride used as adjuvant per mole of n-butane.
**= Catalyst activated at 500° C. (all other runs at 400° C.)
***= Feed introduced at top of Jerguson gauge.
****= Feed introduced at bottom of Jerguson gauge.

TABLE 11

| Catalyst Prep. | Ex. II | Ex. IV | Ex. IV | Ex. VII** | Ex. XV** | Ex. XV** | Ex. IV** |
|---|---|---|---|---|---|---|---|
| Temperature °C. | 120 | 120 | 120 | 80 | 80 | 80 | 80 |
| Pressure, psig. | 500 | 500 | 500 | 250 | 250 | 250 | 250 |
| Wt. % Na (ignited) | 0.26 | 1.38 | 0.3 | 0.6 | 0.82 | 0.9 | 0.76 |
| Wt. % Ce (ignited) | — | 12.4 | 13.5 | 1.72 | —*** | —**** | 13.5 |
| Wt. % La (ignited) | — | — | — | — | 12.3 | **** | — |
| Wt. % N (before activation) | 6.42 | 0.98 | 0.66 | 5.20 | 1.18 | 0.57 | 0.86 |
| Wt. % Ignition Loss | 30.25 | 24.24 | 25.84 | 28.41 | 25.25 | 24.95 | 24.70 |
| Wt. % $C_5^+$ Paraffin Yield* | 109.5 | 119.3 | 75.3 | 26.0 | 68.4 | 142.4 | 132.0 |
| Wt. % $C_5^+$ Unsaturate Yield* | 2.8 | 5.6 | 1.1 | 10.9 | 0.13 | 0.13 | 0.26 |
| $C_5^+$ Paraffin Dist. | | | | | | | |
| Mole % $C_9^+$ | 19.7 | 11.5 | 11.2 | 27.2 | 5.4 | 3.6 | 8.0 |
| $C_8$ | 42.5 | 50.3 | 72.0 | 57.9 | 81.0 | 60.0 | 69.0 |
| $C_7$ | 9.5 | 9.0 | 8.6 | 5.8 | 5.9 | 4.1 | 6.1 |
| $C_6$ | 9.7 | 8.4 | 2.2 | 5.8 | 4.4 | 3.1 | 5.2 |
| $C_5$ | 18.6 | 20.7 | 6.0 | 3.3 | 3.2 | 29.2 | 11.7 |
| $C_8$ Paraffin Dist. | | | | | | | |
| Mole % Trimethylpentanes | 72.0 | 73.1 | 75.0 | 55.1 | 89.0 | 88.4 | 88.0 |
| Mole % Dimethylhexanes | 27.2 | 25.7 | 23.8 | 41.4 | 11.0 | 11.6 | 12.0 |
| Mole % Methylheptanes | 0.7 | 1.2 | 1.2 | 3.5 | 0.0 | 0.0 | 0.0 |
| Mole % $TMP/DMH_x$ | 2.64 | 2.84 | 3.15 | 1.33 | 8.06 | 7.65 | 7.30 |

\* = Based on weight of olefin charged.
\*\* = t-Butyl chloride adjuvant. Olefin and paraffin entered bottom of Jerguson gauge.
\*\*\* = Catalyst prepared from La(NO₃) solution.
\*\*\*\* = Catalyst prepared from mixed rare earth nitrate solution and analyzed 13.8% total rare earth metals (ignited).

TABLE 12

| Salt Used for Exchange Solution | Catalyst Content of Rare Earth Metals (g. ion/100 g. anhydrous cat.) | $C_5^+$ Paraffin Yield (wt. % olefin charge) |
|---|---|---|
| Ce(NO₃)₃ | 0.286 | 132.0 |
| CeCl₃ | 0.272 | 73.1 |
| La(NO₃)₃ | 0.275 | 68.4 |
| LaCl₃ | 0.250 | 112.0(a) |
| RE(NO₃)₃ | 0.301 | 142.4 |
| RECl₃ | 0.236 | 103.1 |
| Gd(NO₃)₃ | 0.305 | 163.0 |

(a) Use of the magnetic drive on the reactor possibly increased this yield as much as 15% over what it would have been with the same packed drive used for the other runs. Even at (112–115 = 98%), its yield vastly exceeds that from La(NO₃)₃.

TABLE 13

ISOPARAFFIN-OLEFIN ALKYLATION WITH ZEOLITE CATALYSTS

Rare Earth Cation and Anion Effects on Catalysts
80° C., 250 psig., i-$C_4$-ane/$C_4$-ene-2 = 14.9 (min.), 3.67 hr.
1.0 g. t-Butyl Chloride

| Salt For Exchange | Ce(NO₃)₃ | CeCl₃ | RE(NO₃)₃ | RECl₃ | La(NO₃)₃ | LaCl₃ |
|---|---|---|---|---|---|---|
| Catalyst Composition | | | | | | |
| Sodium, wt. % (ignited residue basis) | 0.76 | 0.78 | 1.17 | 0.89 | 0.82 | 1.09 |
| Rare Earth, wt. % (ignited residue basis) | 13.5 | 12.9 | 14.2 | 11.2 | 13.1 | 11.9 |
| Run Number (467-) | 830 | 822 | 820 | 854 | 818 | 858 |
| $C_5^+$ Paraffin, wt. % chg. | 132.0 | 73.1 | 142.4 | 103.1 | 68.4 | 112.0 |
| $C_5^+$ Unsaturates, wt. % olefin chg. | 0.26 | 0.15 | 0.13 | 0.77 | 0.13 | 0.16 |
| $C_5^+$ Paraffin Distribution | | | | | | |
| $C_9^+$, mole % | 8.0 | 6.5 | 3.6 | 10.6 | 5.4 | 8.1 |
| $C_8$, mole % | 69.0 | 78.1 | 60.0 | 66.9 | 81.0 | 61.7 |
| $C_7$, mole % | 6.1 | 5.7 | 4.1 | 6.7 | 5.9 | 6.4 |
| $C_6$, mole % | 5.2 | 4.1 | 3.1 | 3.9 | 4.4 | 4.4 |
| $C_5$, mole % | 11.7 | 5.5 | 29.2 | 11.9 | 3.2 | 19.5 |
| $C_8$ Paraffin Distribution | | | | | | |
| TMP, mole % | 88.0 | 88.6 | 88.4 | 84.8 | 89.0 | 86.2 |
| $DMH_x$, mole % | 12.0 | 11.4 | 16.6 | 15.2 | 11.0 | 13.8 |
| $MH_p$, mole % | 0.0 | 0.0 | 0.0 | 0.0 | 0.0 | 0.0 |
| $TMP/DMH_x$ Ratio | 7.30 | 7.74 | 7.65 | 5.09 | 8.06 | 6.25 |

TABLE 14

ISOPARAFFIN-OLEFIN ALKYLATION WITH ZEOLITE CATALYSTS

Catalyst Cerium-Sodium Effects on Alkylation
80° C., 250 psig., i-$C_4$-ane/$C_4$-ene-2 = 14.9 (min.), 3.67 hr
1.0 g. t-Butyl Chloride

| Catalyst Composition | | | | | | |
|---|---|---|---|---|---|---|
| Sodium, wt. % (ignited residue basis) | 0.23 | 0.76 | 1.68 | 2.76 | 1.68 | 1.24 |
| Cerium, wt. % (ignited residue basis) | 13.7[a] | 13.5[a] | 12.8[a] | 13.0 | 8.3[a] | 2.0 |
| Run Number (467-) | 852 | 830 | 848 | 850 | 846 | 828 |
| $C_5^+$ Paraffin, wt. % olefin charge | 135.2 | 132.0 | 115.4 | 118.9 | 62.7 | 26.0 |
| $C_5^+$ Unsaturates, wt. % olefin charge | 0.32 | 0.26 | 0.42 | 0.77 | 4.52 | 10.85 |
| $C_5^+$ Paraffin Distribution | | | | | | |
| $C_9^+$, mole % | 8.4 | 8.0 | 10.6 | 10.1 | 19.1 | 27.2 |
| $C_8$, mole % | 66.0 | 69.0 | 63.4 | 72.8 | 65.1 | 57.9 |
| $C_7$, mole % | 6.6 | 6.1 | 6.7 | 7.2 | 7.4 | 5.8 |
| $C_6$, mole % | 4.9 | 5.2 | 5.5 | 5.7 | 6.0 | 5.8 |
| $C_5$, mole % | 14.1 | 11.7 | 13.9 | 4.1 | 3.4 | 3.3 |
| $C_8$ Paraffin Distribution | | | | | | |
| TMP, mole % | 87.5 | 88.0 | 85.7 | 87.2 | 82.9 | 55.1 |
| $DMH_x$, mole % | 12.4 | 12.0 | 14.3 | 12.8 | 16.2 | 41.4 |
| $MH_p$, mole % | 0.1 | 0.0 | 0.0 | 0.0 | 0.9 | 3.5 |
| TMP/$DMH_x$ Ratio | 7.08 | 7.30 | 6.00 | 6.80 | 5.10 | 1.33 |

[a] = By X-ray fluorescence. Others were by gravimetry.

TABLE 21

Helium and Hydrogen versus Air Activation at 400° C.
$NH_4^+$-, $Ce^{3-}$ Type Y Base 80° C. autogeneous pressure,
i-$C_4$-ane/$C_4$-ene-2 = 15 (min.), 3.67 hr., 1.0 g. TBC

| Activation Gas | Air | Air | $H_2$ | He |
|---|---|---|---|---|
| Run No. | 654 | 656 | 658 | 660 |
| $C_5^+$ Paraffin Yield, wt. % OC | 142.6 | 139.7 | 148.8 | 160.6 |
| $C_5^+$ Unsaturates, wt. % OC | 0.00 | 0.05 | 0.00 | 0.14 |
| $C_5^+$ Paraffin Distribn., mole % | | | | |
| $C_9^+$ | 9.2 | 9.1 | 8.1 | 7.8 |
| $C_8$ | 66.8 | 66.1 | 69.2 | 70.5 |
| $C_7$ | 6.4 | 6.2 | 6.7 | 5.8 |
| $C_6$ | 6.2 | 5.8 | 5.7 | 5.9 |
| $C_5$ | 11.4 | 12.9 | 10.3 | 9.9 |
| $C_8$ Paraffin Distribn. | | | | |
| TMP | 85.6 | 86.4 | 86.7 | 87.5 |
| $DMH_x$ | 14.4 | 13.5 | 13.1 | 12.4 |
| $MH_p$ | 0.0 | 0.2 | 0.2 | 0.0 |
| TMP Distribn. | | | | |
| 2,2,4- | 22.3 | 23.8 | 25.8 | 26.8 |
| 2,2,3- | 5.0 | 5.3 | 5.3 | 5.4 |
| 2,3,4- | 33.9 | 32.3 | 31.1 | 30.4 |
| 2,3,3- | 38.9 | 38.7 | 37.8 | 37.3 |

TABLE 22

Liquid Phase Isoparaffin-Olefin Alkylation with Solid Zeolite Catalysts
Gadolinium versus Ammonium versus Cerium and Type X versus Type Y Zeolite
Autogenous pressure, 80° C., i-$C_4$-ane/$C_4$-ene-2 = 15 (min.), 3.67 hr.,
1.0 g. tertiary butyl chloride adjuvant

| Catalyst | | | | | |
|---|---|---|---|---|---|
| Zeolite before activation | $GdNH_4Y$ | $GdNH_4Y$ | $NH_4Y$ | $CeNH_4X^*$ | $CeNH_4Y$ |
| Activation (400° C.) Gas | Air | He | Air | Air | Air |
| Run No. | 628 | 674 | 596 | 622 | 642 |
| $C_5^+$ Paraffin Yield, wt. % OC | 163.0 | 169.8 | 43.5 | 130.0 | 161.6 |
| $C_5^+$ Unsaturates, wt. % OC | 0.00 | 0.05 | 0.2 | 0.0 | 0.00 |
| $C_5^+$ Paraffin Distribution, mole % | | | | | |
| $C_9^+$ | 3.7 | 5.8 | 18.9 | 8.3 | 5.4 |
| $C_8$ | 67.6 | 71.4 | 54.3 | 59.0 | 71.2 |
| $C_7$ | 5.7 | 7.7 | 6.2 | 4.8 | 7.4 |
| $C_6$ | 4.4 | 5.7 | 7.0 | 4.0 | 5.9 |
| $C_5$ | 18.5 | 9.3 | 13.6 | 23.9 | 10.0 |
| $C_8$ Paraffin Distribution | | | | | |
| TMP | 88.1 | 88.2 | 59.3 | 85.7 | 85.9 |
| $DMH_x$ | 11.9 | 11.8 | 38.7 | 14.2 | 14.1 |
| $MH_p$ | 0.0 | 0.0 | 2.0 | 0.1 | 0.0 |
| TMP Distribution | | | | | |
| 2,2,4- | 27.4 | 28.4 | 13.6 | 15.5 | 24.4 |
| 2,2,3- | 5.9 | 5.4 | 5.1 | 4.1 | 5.6 |
| 2,3,4- | 28.8 | 29.1 | 39.6 | 34.0 | 32.0 |
| 2,3,3- | 37.9 | 37.1 | 41.7 | 46.4 | 38.0 |
| Catalyst Analysis (ignited basis, before activation) | | | | | |
| Wt. % Na | 0.97 | 0.97 | 1.05 | 0.93 | 0.97 |
| Wt. % Ce or Gd | 14.39 Gd | 14.39 Gd | — | 15.5 Ce | 13.99 Ce |
| Wt. % N | 1.09 | 1.09 | 5.86 | 1.85 | 0.84 |
| Wt. % loss on ignition | 25.35 | 25.35 | 29.67 | 25.47 | 26.28 |
| Analysis of Base Na zeolite (before exchange, ignited basis) | | | | | |
| Wt. % Na | 9.51 | 9.51 | — | — | 9.42 |
| Wt. % $Al_2O_3$ | 16.56 | 16.56 | — | — | 16.32 |
| Wt. % $SiO_2$ | 45.29 | 45.29 | — | — | 47.87 |

TABLE 22-continued

Liquid Phase Isoparaffin-Olefin Alkylation with Solid Zeolite Catalysts

Gadolinium versus Ammonium versus Cerium and Type X versus Type Y Zeolite

Autogenous pressure, 80° C., i-$C_4$-ane/$C_4$-ene-2 = 15 (min.), 3.67 hr., 1.0 g. tertiary butyl chloride adjuvant

| Wt. % loss of ignition | 24.32 | 24.32 | — | — | 25.05 |

*Base $CeNH_4X$ zeolite analyzed 37.56% $SiO_2$ (17.56% Si), Al/Si atomic ratio was 0.69

TABLE 23

ANALYSIS OF $C_{5+}$ LIQUID PRODUCT OBTAINED FROM CeHY CATALYST, 600° C. ACTIVATION

| Paraffin Fraction | Distribution (Mole %) |
|---|---|
| $C_{9+}$ | 10.1 |
| $C_8$ | 69.4 |
| $C_7$ | 6.9 |
| $C_6$ | 6.0 |
| $C_5$ | 7.5 |

$C_{5+}$ paraffin yeild (based on wt % olefin charged) was 128.5

The Run was made in stirred, batch reactor.

The invention claimed is:

1. An isoparaffin-olefin alkylation process wherein $C_4$-$C_6$ isoparaffin is contacted under alkylation conditions with $C_2$-$C_9$ olefin and the catalyst comprising a three dimensional crystalline zeolite molecular sieve having a pore size large enough to adsorb 2,2,3-trimethylpentane and having a composition expressed in terms of mole ratios of oxides as $$a(I_2O):b(IIO):c(III_{\frac{2}{3}}O):d(IV_{\frac{1}{2}}O):Al_2O_3:eSio_2$$

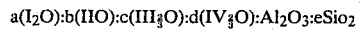

wherein I represents a monovalent metal cation; II represents a divalent metal cation; III represents a trivalent metal cation; IV represents a tetravalent cation; a has a value of from zero to 0.15; b has a value of from zero to 0.75; c and d each have values of from zero to 1; e has a value of from 2 to 20; with the proviso that when e has a value of from 2 to 3, the value of (b+c)=0.75 to 1 and d=0; and with the proviso that when e has a value of >3 to 4, the value of (b+c+d)=0.6 to 1.0; and with the further proviso that when e has a value of >4 to 20, the value of (b+c+d)0.25 to 1.0, said zeolite containing less than about 60 percent of the water content when measured after it has been heated to about 570° F.

2. Process according to claim 1 wherein the zeolite contains less than 40 percent of the water content when measured after it has been heated to about 570° F.

3. Process of claim 1 wherein III consists essentially of cations of a trivalent rare earth metal or of a mixture of two or more rare earth metals.

4. Process of claim 3 wherein said rare earth metal consists mainly of lanthanum, cerium, gadolinium, dysprosium or samarium.

5. Process of claim 4 wherein a has a value of about 0.1.

6. Process of claim 1 wherein said coefficient a is in the range of 0 to 0.1, b is about 0, c is in the range of 0.4 to 0.8, and d is about 0.

7. Process of claim 6 wherein e is about 4.7.

8. An isoparaffin alkylation process which comprises contacting $C_4$-$C_6$ isoparaffin with an olefin containing from 2 to 9 carbon atoms inclusive and a catalyst comprising a three dimensional crystalline zeolite molecular sieve having a pore size large enough to adsorb 2,2,3-trimethylpentane and having a composition expressed in terms of mole ratios of oxides as $$a(I_2;b(IIO):c(III_{\frac{2}{3}}O):d(IV_{\frac{1}{2}}O:Al_2O_3:eSiO2$$

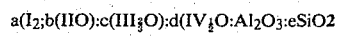

wherein I represents a monovalent metal cation; II represents a divalent metal cation; III represents a trivalent metal cation; IV represents a tetravalent cation; a has a value of from zero to 0.15; b has a value of from zero to 0.75; c and d each have values of from zero to 1; e has a value of from 2 to 20; with the proviso that when e has a value of from 2 to 3, the value of (b+c)=0.75 to 1 and d=O; and with the proviso that when e has a value of 3 to 4, the value of (b+c+d)=0.6 to 1.0; and with the further proviso that when e has a value of 4 to 20 the value of (b+c+d)=0.25 to 1.0, said zeolite containing less than about 60 percent of the water content when measured after it has been heated to about 570° F., said content of catalyst, isobutane and olefin being at a temperature from about 25°–120° C. and at a pressure commensurate therewith to maintain at least the isoparaffin in the liquid state.

9. Process of claim 8 wherein said isoparaffin is isobutane.

10. Process of claim 9 wherein said contacting is at a mean residence time in the range of 0.05–0.5 hour.

11. Process of claim 9 wherein said contacting is at a molar ratio of isobutane to olefin of at least about 5:1.

12. The process of claim 11 wherein said zeolite contains less than 40 percent of the water content when measured after it has been heated to about 570° F.

13. The process of claim 11 wherein, in said catalyst, III consists essentially of cations of a trivalent rare earth metal or of a mixture of two or more rare earth metals.

14. Process of claim 13 wherein a has a value of about 0.1.

15. The process of claim 13 wherein said rare earth metal consists essentially of gadolinium and wherein said zeolite is at least 50% crystalline and can adsorb benzene.

16. The process of claim 15 wherein said zeolite on an ignited basis contains less than 1 wt. % Na, at least 14 wt. % Gd, and has a Type Y framework.

17. Process of claim 1 wherein the catalyst activity appreciably decreases during the course of the reaction, after which time the catalyst is separated from the hydrocarbon reactants and is regenerated.

18. Process of claim 17 wherein said regeneration comprises burning in air.

19. An isoparaffin alkylation process which comprises contacting $C_4$-$C_6$ isoparaffin with an olefin containing from 2 to 9 carbon atoms inclusive and a catalyst comprising a three dimensional crystalline zeolite molecular sieve having a pore size large enough to adsorb 2,2,3-trimethylpentane and having a composition expressed in terms of mole ratios of oxides as $$a(I_2O:b(IIO):C(III_{\frac{2}{3}}O):d(IV_{\frac{1}{2}}0):Al_2O_3:eSiO_2$$

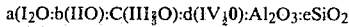

wherein I represents a monovalent metal cation; II represents a divalent metal cation; III represents a trivalent metal cation; IV represents a tetravalent cation; a has a value of from zero to 0.15; b has a value of from zero to 0.75; c and d each have values of from zero to 1; e has a value of from 2 to 20; with the proviso that when e has a value of from 2 to 3, the value of (b+c)=0.75 to 1 and d=O; and with the proviso that when e has a value of 3 to 4, the value of (b+c+d)=0.6 to 1.0; and with the further proviso that when e has a value of 4 to 20, the value of (b+c+d)=0.25 to 1.0, said zeolite containing less than about 60 percent of the water content when measured after it has been heated to about 570° F., said contact of catalyst, isoparaffin and olefin being at a temperature of from about 25°-120° C. and at a pressure commensurate therewith to maintain at least the isoparaffin in the liquid state an controlling the addition of said olefin reactant such that the amount of unreacted feed olefin in the reaction mixture is maintained at less than 12 mole percent based on unreacted isoparaffin.

20. Process according to claim 19 wherein said contacting is stopped after substantial alkylation has occured but before the weight rate or production of unsaturated hydrocarbon becomes greater than the weight ratio of production of saturated hydrocarbon.

21. The process of claim 19 wherein said isoparaffin is isobutane.

* * * * *